(12) United States Patent
Xu et al.

(10) Patent No.: US 9,888,689 B2
(45) Date of Patent: *Feb. 13, 2018

(54) COMPOSITIONS CONTAINING A PYRIPYROPENE INSECTICIDE AND AN ADJUVANT

(75) Inventors: Wen Xu, Cary, NC (US); Paul Neese, Apex, NC (US); William Maurice Fletcher, Bahama, NC (US); Douglas D. Anspaugh, Apex, NC (US); Heidi Emilia Saxell, Vantaa (FI); Cedric Dieleman, Scheibenhard (FR); Walter Weishaar, Gruenstadt (DE); Paul Ch. Kierkus, Wake Forest, NC (US); Kara Benton, Holly Springs, NC (US); Rainer Berghaus, Speyer (DE); Tatjana Levy, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/822,514

(22) PCT Filed: Sep. 13, 2011

(86) PCT No.: PCT/EP2011/065855
§ 371 (c)(1),
(2), (4) Date: Mar. 12, 2013

(87) PCT Pub. No.: WO2012/035015
PCT Pub. Date: Mar. 22, 2012

(65) Prior Publication Data
US 2013/0190360 A1    Jul. 25, 2013

Related U.S. Application Data

(60) Provisional application No. 61/382,507, filed on Sep. 14, 2010, provisional application No. 61/382,518, (Continued)

(30) Foreign Application Priority Data

Sep. 14, 2010  (EP) .................................... 10176596
Sep. 14, 2010  (EP) .................................... 10176625

(51) Int. Cl.
*A01N 43/90* (2006.01)
*A01N 53/00* (2006.01)
(Continued)

(52) U.S. Cl.
CPC .............. *A01N 43/90* (2013.01); *A01N 53/00* (2013.01)

(58) Field of Classification Search
CPC ........ A01N 43/90; A01N 53/00; A01N 25/22; A01N 25/30; A01N 25/02
(Continued)

(56) References Cited

U.S. PATENT DOCUMENTS 3,948,636 A    4/1976 Marks
5,089,259 A    2/1992 Wessling et al.
(Continued)

FOREIGN PATENT DOCUMENTS

CA    2 609 527    12/2006
EP    1 889 540    2/2008
(Continued)

OTHER PUBLICATIONS

Narayanan, K. S. Macro and microemulsion technology and trends. In Pesticide Formulation and Adjuvant Technology; Foy, C. L. and Pritchard, D. W. Eds.; CRC Press, Boca Raton, FL, 1996; pp. 148-164.*

(Continued)

*Primary Examiner* — Irina Neagu
(74) *Attorney, Agent, or Firm* — Brinks Gilson & Lione

(57) ABSTRACT

The present invention relates to a compositions comprising a pyripyropene pesticide of the formula (I) or (II) as defined below

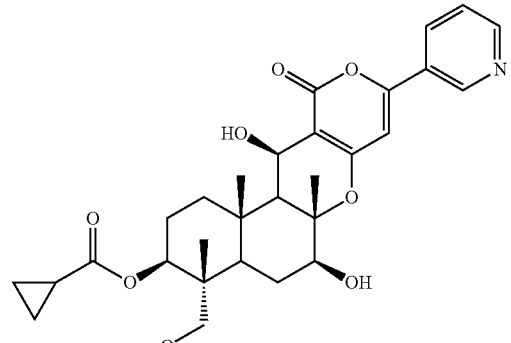

Formula I

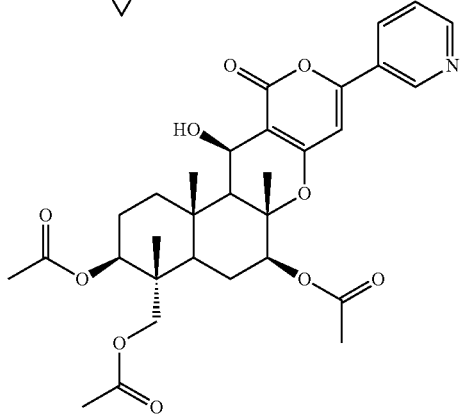

Formula II and an adjuvant.

(Continued)

Figure 1:
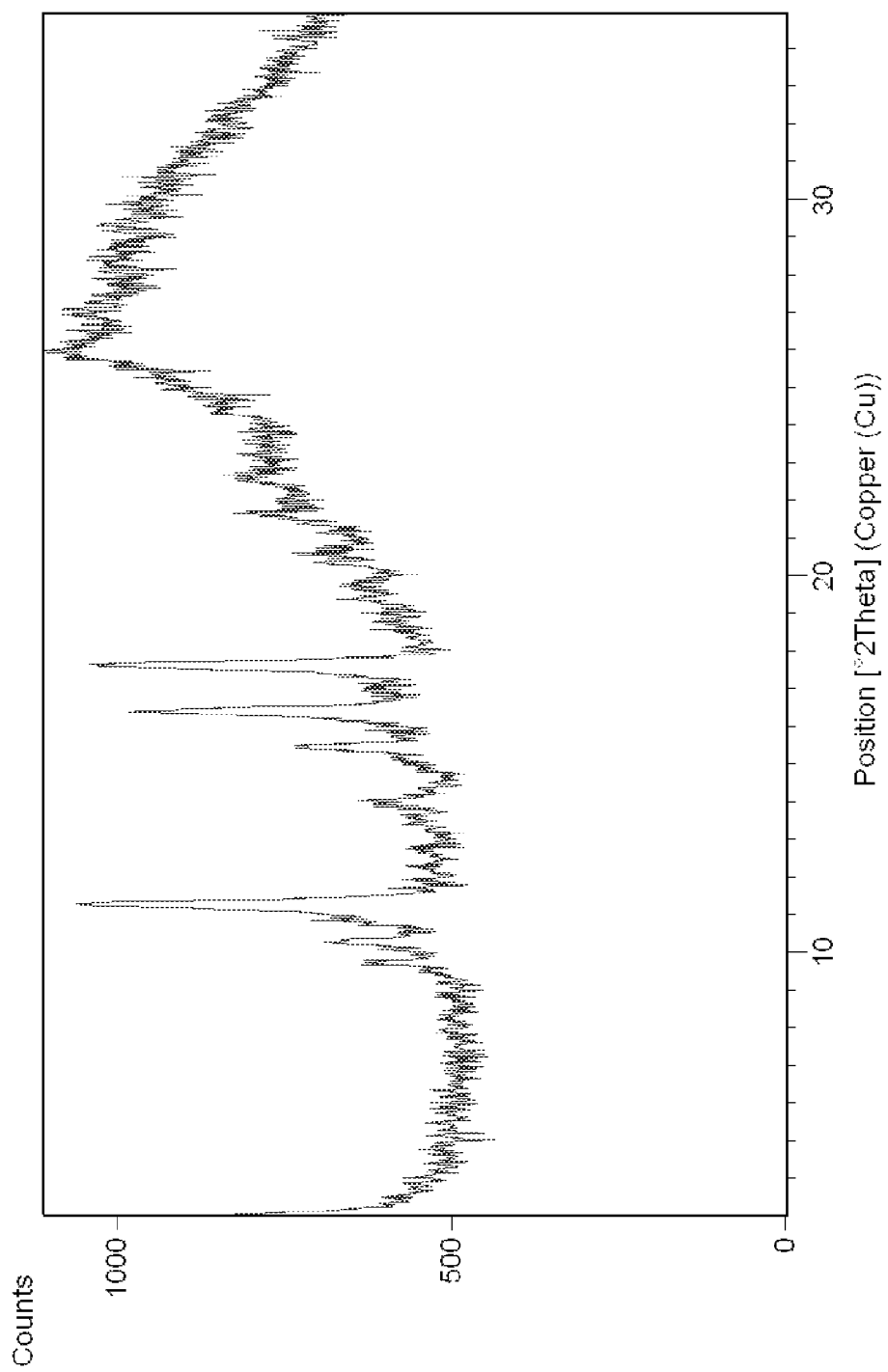

The present invention relates also to methods of preparing and applying such compositions, as well as several uses thereof, and finally seeds, comprising said composition.
The invention also relates to an aqueous pesticide formulation comprising a pesticide compound of the formula I as defined in claim 1 in the form of fine particles suspended in an aqueous liquid.

25 Claims, 3 Drawing Sheets

Related U.S. Application Data filed on Sep. 14, 2010, provisional application No. 61/426,537, filed on Dec. 23, 2010, provisional application No. 61/426,540, filed on Dec. 23, 2010.

(51) Int. Cl.
*A01N 25/22* (2006.01)
*A01N 25/30* (2006.01)
*A01N 25/02* (2006.01)

(58) Field of Classification Search
USPC .............. 251/251, 292; 546/283.1; 549/384
See application file for complete search history.

(56) References Cited

U.S. PATENT DOCUMENTS

| | | | |
|---|---|---|---|
| 5,807,721 | A | 9/1998 | Omura et al. |
| 6,495,595 | B2 | 12/2002 | Moore et al. |
| 6,521,785 | B2 | 2/2003 | Shannon et al. |
| 6,706,666 | B2 | 3/2004 | Hasebe et al. |
| 7,241,454 | B2 | 7/2007 | Warrington et al. |
| 7,268,259 | B1 | 9/2007 | Behler et al. |
| 7,491,738 | B2 | 2/2009 | Goto et al. |
| 2004/0106523 | A1 | 6/2004 | Stridde et al. |
| 2004/0157743 | A1 | 8/2004 | Rosenfeldt et al. |
| 2006/0165748 | A1 | 7/2006 | Arimoto |
| 2008/0096763 | A1 | 4/2008 | Dawson et al. |
| 2008/0300313 | A1 | 12/2008 | Byrne et al. |
| 2008/0312290 | A1 | 12/2008 | Vermeer et al. |
| 2010/0281584 | A1 | 11/2010 | Horikoshi et al. |
| 2012/0046470 | A1 | 2/2012 | Fukuda et al. |
| 2013/0184153 | A1* | 7/2013 | Dieleman et al. ............ 504/100 |
| 2013/0190360 | A1 | 7/2013 | Xu et al. |
| 2014/0142289 | A1 | 5/2014 | Anzai et al. |
| 2014/0371178 | A1 | 12/2014 | Horikoshi et al. |

FOREIGN PATENT DOCUMENTS

| | | |
|---|---|---|
| EP | 2 036 437 | 3/2009 |
| EP | 9 107 060 | 10/2009 |
| EP | 2 119 361 | 11/2009 |
| EP | 2 186 815 | 5/2010 |
| EP | 2 223 599 | 9/2010 |
| JP | 2993767 | 10/1999 |
| JP | 2002-522400 | 7/2002 |
| JP | 2002-532464 | 10/2002 |
| JP | 200815344 | 6/2005 |
| WO | WO 94/09417 | 4/1994 |
| WO | WO 1994009147 | 4/1994 |
| WO | WO 98/35553 | 8/1998 |
| WO | WO 00/07709 | 2/2000 |
| WO | WO 00/35863 | 6/2000 |
| WO | WO 2004/060065 | 7/2004 |
| WO | WO 2006/129714 | 12/2006 |
| WO | WO 2007/117001 | 10/2007 |
| WO | WO 2008/013336 | 1/2008 |
| WO | WO 2008/108491 | 9/2008 |
| WO | WO 2009/081851 | 7/2009 |
| WO | WO 2010010955 | 1/2010 |
| WO | WO 2010/131676 | 11/2010 |
| WO | WO 2011/113052 | 9/2011 |
| WO | WO 2011/147952 | 9/2011 |
| WO | WO 2011/147953 | 12/2011 |
| WO | WO 2012/035010 | 3/2012 |
| WO | WO 2013/135604 | 9/2013 |
| WO | WO 2013/135605 | 9/2013 |
| WO | WO 2013/135606 | 9/2013 |
| WO | WO 2013/135610 | 9/2013 |

OTHER PUBLICATIONS

Sunazuka, Toshiaki, et al., "Synthetic Study of α-Pyrone Meroterpenoids, Pyripyropens", Journal of Society of Synthetic Organic Chemistry, 1998, pp. 478-488, vol. 56, No. 6.
Omura, Satoshi, et al., "Pyripyropense, highly potent inhibitors of Acyl-CoA: Cholesterol Acyltransferase produced, by *Aspergillus fumigatus*", Journal of Antibiotics, 1993, p. 1168-9, vol. 46, No. 7.
Wang, Hui-Juan, et al., Aflavinines and Other Antiinsectan Metabolites from the Ascostromata of *Eupenicillium crustaceum* and related Species, Applied and Environmental Microbiology, 1995, p. 4429-35, vol. 61, No. 12.
International Search Report dated Dec. 20, 2011, prepared in International Application No. PCT/EP2011/065855.
International Preliminary Report on Patentability dated Nov. 20, 2012, prepared in International Application No. PCT/EP2011/065855.
Office Action dated Oct. 1, 2014 in U.S. Appl. No. 13/822,530.
Wang, C.J., et al. "Foliar uptake of pesticides—present status and future challenge", Pesticide Biochemistry and Physiology, 2007, p. 1-8, vol. 87.
Unknown Author, "Noyaku Seizai Gaido", Japan Plant Protection Association, 1997, pp. 26-31 and 104-112, Pesticide Science Society of Japan, Special Committees on Agricultural Formulation and Application.
Office Action dated Apr. 20, 2015 in U.S. Appl. No. 13/822,530.
Office Action dated Jul. 13, 2015 in U.S. Appl. No. 14/383,661.
Final Office Action dated May 17, 2016 in U.S. Appl. No. 13/822,530.
Office Action dated Apr. 20, 2016 in U.S. Appl. No. 14/383,756.
Office Action dated Jan. 5, 2017 in U.S. Appl. No. 14/383,731.
Office Action dated 2017—Mar. 14, 2017 from U.S. Appl. No. 14/383,665, filed Sep. 8, 2014.
Office Action dated Mar. 31, 2017 from U.S. Appl. No. 14/383,756, filed Sep. 8, 2014.
Office Action dated Sep. 8, 2016 in U.S. Appl. No. 14/383,665.
Office Action dated Sep. 7, 2017 from U.S. Appl. No. 14/383,665, filed Sep. 8, 2014.

* cited by examiner

COMPOSITIONS CONTAINING A PYRIPYROPENE INSECTICIDE AND AN ADJUVANT

This application is a National Stage application of International Application No. PCT/EP2011/065855, filed Sep. 13, 2011, which claims the benefit of U.S. Provisional Application No. 61/382,507, filed Sep. 14, 2010; U.S. Provisional Application No. 61/382,518, filed Sep. 14, 2010; U.S. Provisional Application No. 61/426,537, filed Dec. 23, 2010; and U.S. Provisional Application No. 61/426,540, filed Dec. 23, 2010, the entire contents of which are hereby incorporated herein by reference. This application also claims priority under 35 U.S.C. §119 to European Patent Application No. 10176596.4, filed Sep. 14, 2010; and European Patent Application No. 10176625.1,filed Sep. 14, 2010, the entire contents of which are hereby incorporated herein by reference.

The present invention relates to a composition comprising a pyripyropene pesticide for the formulae I or II as defined below and an adjuvant. The present invention also relates to a pesticidal formulation in the form of a suspension concentrate. The present invention also relates to crystalline hydrates of the pyripyropene pesticide of the formula I as defined below.

When preparing agrochemical formulations of pesticidal compounds different problems can be encounter. One problem may be that the pesticidal activity of the pesticidal active compound may be affected in some way in the agrochemical formulation. Thus one disadvantage of known agrochemical formulations of pesticides is an affected and potentially lower pesticidal, for example insecticidal, activity of the pesticidal active ingredient in such agrochemical formulation.

The pyripyropene pesticide of formula (I)

(Formula I)

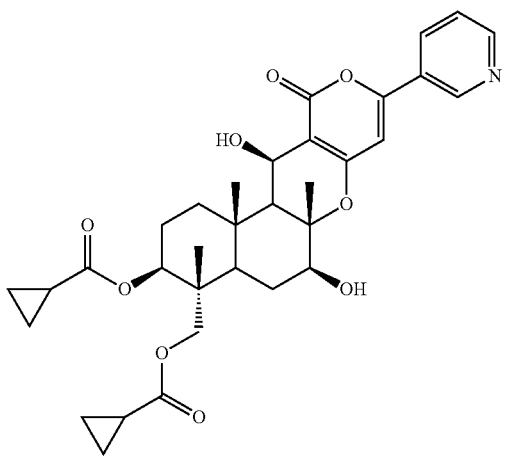

(in the following also called "Insecticide A") is known from WO 2009/081851 (Examples, compound 4) and belongs to the class of pyripyropene derivatives.

WO 2009/081851 discloses various agrochemical formulations of Insecticide A and useful additives for agrochemical formulations of it.

EP 2 119 361 and EP 1 889 540 disclose various agrochemical formulations of pyripyropene derivatives and useful additives for agrochemical formulations of it.

The pyripyropene pesticide of formula (I) may be prepared by the process described in WO 2006/129714 or EP 2 186 815.

Pyripyropene A (pyripyropene pesticide of formula II herein below), produced e.g. by the method described in Journal of Society of Synthetic Organic Chemistry, Japan (1998), Vol. 56, No. 6, pp. 478-488 or WO 94/09417, may for example be used as starting material for preparing further pyripyropene derivatives.

(Formula II)

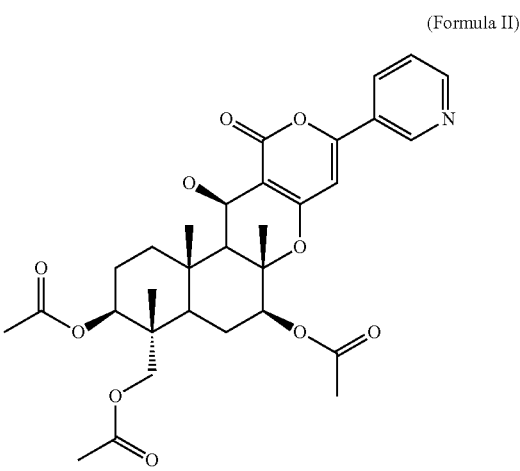

Pyripyropene A (in the following also called "Insecticide B") has inhibitory activity against ACAT (acyl-CoA: cholesterol acyltransferase) and is expected to be applied, for example, for the treatment of diseases induced by cholesterol accumulation, as described in Japanese Patent No. 2993767 (Japanese Patent Laid-Open Publication No. 360895/1992) and Journal of Antibiotics (1993), 46(7), 1168-9.

Furthermore, Applied and Environmental Microbiology (1995), 61(12), 4429-35 describes that pyripyropene A ("Insecticide B") itself has insecticidal activity against larvae of *Helicoverpa zea*. Furthermore, WO 2004/060065 describes that pyripyropene A has insecticidal activity against *Plutella xylostella* L larvae and *Tenebrio molitor* L.

When trying to provide agricultural formulations of pyripyropene derivatives, in particular pyripyropene derivatives of formulae I or II, one faces several problems. One problem associated with pyripyropene derivatives of the formulae I and II is their poor formulation stability in aqueous formulations and the poor dilution stability of the formulations, which may result in settling or agglomeration of the active ingredient particles. Another problem one may encounter is that the pesticidal activity of the pesticidal active compound may be affected negatively in some way in the agrochemical formulation. Thus a further disadvantage of agrochemical formulations and compositions of pyripyropene derivatives of formulae I or II, is an affected and potentially lower insecticidal, activity of the pyripyropene derivatives of formulae I or II.

One object of the present invention is therefore to find a way to stabilize, to improve, to increase and/or to prolong the pesticidal activity of pyripyropene derivatives of the formulae I and II in an agrochemical formulations. A further object of the present invention is to provide a superior formulation stability of pyripyropene derivates in aqueous formulations, in particular in aqueous suspension concentrate formulations.

The improvement of the insecticidal activity of pyripyropene of the formula I in agrochemical formulations is another aspect of the present invention. The development of a novel pest control composition comprising pyripyropene of the formula I itself having effective insecticidal activity is desirable. Therefore, it is an object of the present invention to find a way to stabilize, to improve, to increase and/or to prolong the insecticidal activity of Insecticide A.

The improvement of the insecticidal activity of insecticide B in agrochemical formulations is a further aspect of the present invention. The development of a novel pest control composition comprising insecticide B as naturally derived insecticide itself having effective insecticidal activity is desirable. Therefore, it was another object of the present invention to find also a way to stabilize, to improve, to increase and/or to prolong the insecticidal activity of insecticide B.

These and further objects are solved by a agrochemical composition comprising a pyripyropene pesticide of the formulae I or II and at least one adjuvant.

The present invention also relates to methods of preparing and applying such compositions, as well as several uses thereof. In particular, the present invention also relates to a method for preparing said composition comprising contacting, in particular mixing, the pyripyropene pesticide of the formulae I or II or an agricultural formulation thereof and the adjuvant.

The invention also relates to a method for preparing an aqueous tank-mix comprising the steps of a) providing a composition containing the pyripyropene pesticide of the formulae I or II; b) providing a composition containing the adjuvant; and c) contacting the compositions of steps a) and b) and water to obtain the aqueous tank-mix.

Furthermore, the invention relates to the use of the adjuvant for increasing the efficacy of the pyripyropene pesticide of the formulae I or II; and to a kit of parts comprising, as separate components, a) the pyripyropene of the formulae I or II, and b) the adjuvant, for combined use.

Further subject matters are a method for protecting plants from attack or infestation by insects, acarids or nematodes comprising contacting the plant, or the soil or water in which the plant is growing, with said composition in pesticidally effective amounts; a method for controlling insects, arachnids or nematodes comprising contacting an insect, acarid or nematode or their food supply, habitat, breeding grounds or their locus with said composition in pesticidally effective amounts; a method for protection of plant propagation material comprising contacting the plant propagation material, preferably seeds, with said composition in pesticidally effective amounts; and finally seed, comprising said composition.

It was also found that pyripyropene pesticide compound of the formula I as described in prior art is difficult to formulate as a stable aqueous formulation, as it tends to form aggregates or coarse particles which tend to settle from the formulation. Apart from that, upon dilution of such aqueous formulations with water, the pesticide compound may settle, separate from the dilution as coarse material, which may lead to a clogging of the spraying equipment or to dosage problems.

It was surprisingly found that these problems can be overcome by the below suspension concentrates of the pyripyropene pesticide compound of the formula I. These concentrates have superior formulation stability, in particular against formation of coarse particles and settling of the active ingredient from the formulation or the aqueous dilution.

The invention also relates to an aqueous pesticide formulation comprising the pyripyropene pesticide compound of the formula I as defined above in the form of fine particles suspended in an aqueous liquid, which comprises
a) 5 to 30 wt %, in particular 6 to 20 wt %, especially 8 to 15 wt %, based on the total weight of the formulation, of the pesticide compound of formula I;
b) 6 to 20 wt %, in particular 8 to 17 wt %, especially 9 to 15 wt %, based on the total weight of the formulation, of an anionic polymeric surfactant having a plurality of $SOS^{3-}$ groups,
c) 0.1 to 10 wt %, in particular 0.5 to 8 wt %, especially 1 to 5 wt %, based on the total weight of the formulation, of a non-ionic surfactant,
d 40 to 88.9%, in particular 55 to 85.5 wt %, especially 65 to 82 wt %, based on the total weight of the formulation, by weight of water.

The term wt %, as used herein, has to be understood as % by weight.

It was also found that the problems associated with aqueous formulations of the compound of formula I may be overcome by certain crystalline hydrates as defined below.

Therefore, a further aspect of the present invention relates to a hydrate A of the compound of formula I, which, in an X-ray powder diffractogram at 25° C. and Cu—$K_\alpha$ radiation, shows at least four, in particular at least 5 or all of the following reflexes, given as 2θ values: 9.7±0.2°, 10.3±0.2°, 11.3±0.2°, 14.0±0.2°, 15.5±0.2°, 16.4±0.2°, 17.6±0.2°.

Yet, a further aspect of the present invention relates to a hydrate B of the compound of formula I, which, in an X-ray powder diffractogram at 25° C. and Cu—$K_\alpha$ radiation, shows at least four, in particular at least 5 or at least 7 or at least 9 or all of the following reflexes, given as 2θ values: 8.0±0.2°, 9.5±0.2°, 10.7±0.2°, 11.0±0.2°, 11.2±0.2°, 11.7±0.2°, 14.2±0.2°, 15.6±0.2°, 16.5±0.2°, 17.7±0.2°, 21.5±0.2°.

Yet, a further aspect of the present invention relates to a hydrate C of the compound of formula I, which, in an X-ray powder diffractogram at 25° C. and Cu—$K_\alpha$ radiation, shows at least four, in particular at least 5 or at least 7 or at least 9 or all of the following reflexes, given as 2θ values: 7.5±0.2°, 9.6±0.2°, 11.0±0.2°, 11.7±0.2°, 12.1±0.2°, 12.5±0.2°, 15.8±0.2°, 16.3±0.2°, 17.4±0.2°, 19.3±0.2° and 19.6±0.2°.

Combinations of preferred embodiments with other preferred embodiments are within the scope of the present invention.

The pesticide may be present in the composition of the invention in any form, such as dissolved, suspended, or emulsified. Preferably the pesticide compound of the formulae I or II is present in the composition in dissolved form or in suspended form. In particular, the composition comprising the adjuvant and the pesticide compound of the formulae I or II is an aqueous composition in the form of a suspension or an emulsion, wherein the pesticide compound of the formulae I or II is present in the form of suspended particles or in the form of emulsified droplets containing the pesticide compound in dissolved form.

Suitable adjuvants are all known materials of this class and are known to an expert, for example from Hazen, Weed Technology, 2000, 14, 773-784 "Adjuvants-terminology, classification and chemistry". Examples are wetter-spreader adjuvants, sticker adjuvants, humectants, or penetration agents. Further examples are surfactants (e.g. nonionic, anionic, cationic or ampohoteric), wetting agents, spreading agents, sticking agents, humectants, penetration agents (e.g. paraffinic or vegetable-derived crop oil concentrates, phytobland oils, emulsifiable crop oil, vegetable oil concentrates, modified vegetable oil). The definitions and examples of the aforementioned terms are given in Hazen (2000).

Preferred examples of adjuvants are listed in Table 1 based on their brand name including their main functional components.

TABLE 1

Adjuvants listed by brand name

| Brand Name | Adjuvant type | Main functional components |
| --- | --- | --- |
| ACCUQUEST ® | Deposition (Drift Control) and/or Retention Agent plus Ammonium Sulfate | Blend of water soluble polymers and ammonia salts, and sequestrants |
| ACCUQUEST ® WM | Deposition (Drift Control) and/or Retention Agent plus Ammonium Sulfate and Defoamer | Proprietary blend of polyhydroxy-carboxylic acids, sulfates, and polymeric deposition agents |
| ACCUZONE ® DC | Deposition (Drift Control) and/or Retention Agent plus Ammonium Sulfate and Defoamer, Water Conditioning Agent | Ammonium and potassium salts plus organic polymers |
| AD-SPRAY ® 80 | Nonionic Surfactant | Alkylarylpolyalkoxylated glycols and derivatives |
| AD-SPRAY ® 90 | Nonionic Surfactant | Proprietary blend of alkylarylpoly-alkoxylated glycols and derivatives |
| AERO DYNE-AMIC ® | Methylated or Ethylated Vegetable Oil, Nonionic Surfactant, Buffering Agent or Acidifier | Proprietary blend of ethoxylated alkyl phosphate esters, polyalkylene modified polydimethylsiloxane, nonionic emulsifiers and methylated vegetable oils |
| AGRI-DEX ® | Crop Oil (Petroleum) Concentrate | Proprietary blend of heavy range paraffin base petroleum oil polyol fatty acid esters polyethoxylated derivatives |
| ALIGN ® | Foam Marker | Nonionic and anionic surfactants, fatty alcohol, and butoxy ethanol |
| BLENDEX ® VHC | Compatibility Agent | Proprietary blend of alkylarylpolyethanol phosphate esters and other ethoxylated derivatives |
| BUFFER EXTRA STRENGTH ® | Buffering Agent or Acidifier | Proprietary blend of alkylarylpolyethoxy-ethanol phosphates and organic phosphatic acids |
| BUFFER PS ® | Buffering Agent or Acidifier | Alkylarylpolyethoxyethanol phosphates and organic phosphatic acids |
| CIDE WINDER ® | High Surfactant Oil Concentrate | Ethoxylated alkyl phosphate esters, nonionic surfactants, and C16-C18 alkanoates |
| CITRUFILM ® | Crop Oil (Petroleum) Concentrate | Light to mid range paraffin base petroleum oil, polyol fatty acid esters, and polyethoxylated derivatives |
| COHORT ® DC | Nonionic Surfactant | Blend of alcohol ethoxylates and organic nitrogen |
| COMBAT ® PLUS | Antifoam Agent | Proprietary dimethylpolysiloxane emulsion |
| COTTON OIL PLUS ® | Vegetable Oil Concentrate, Deposition (Drift Control) and/or Retention Agent, Buffering Agent or Acidifier | Cottonseed oil plus nonionic blend of alkoxylated alkylated alkylphenols and fatty acids (85:15) |
| CROP OIL CONCENTRATE ® | Crop Oil (Petroleum) Concentrate | Paraffin based petroleum oil plus polyoxyethylated polyol fatty acid esters, and polyol fatty acid esters (83:17) |
| DROP ZONE ® LC | Deposition (Drift Control) and/or Retention Agent, Crop Oil (Petroleum) Concentrate | Guar gum dispersed in paraffin oil |
| DYNA-PAK ® | Surfactant plus Nitrogen Source | Alkanoates, nonionic surfactants, and carbamide salts |
| DYNE-AMIC ® | Methylated or Ethylated Vegetable Oil, Organo-Silicone Surfactant, Nonionic Surfactant | Proprietary blend of polyethoxlated dimethyl siloxanes, alkylaryl ethoxylates and methylated seed oils |

TABLE 1-continued

Adjuvants listed by brand name

| Brand Name | Adjuvant type | Main functional components |
|---|---|---|
| FOAMBUSTER ® | Antifoam Agent | Dimethylpolysiloxane |
| FOAMER ® | Foam Marker | Sodium alpha-olefin sulfonate |
| GROUNDED ® | Deposition (Drift Control) and/or Retention Agent | Proprietary blend of aliphatic hydrocarbons, hexahydric alcohol ethoxylated and fatty acids |
| HEL-FIRE ® | Deposition (Drift Control) and/or Retention Agent, Water Conditioning Agent | Aminated phosphoric and carboxylic acids, sulphurated amides and spray depostion aids |
| HYPER-ACTIVE ® | Other | Dialkyldimethyl ammonium polynapthyl amine plus polyethoxylated alkylaryl ethers |
| INDUCE ® | Nonionic Surfactant | Alkylarylpolyoxyalkane ether and free fatty acids |
| INDUCE ® PH | Nonionic Surfactant | Proprietary blend of alkylarylpoly-oxylkane ethers, alkylarylpolyethoxy-ethanol phosphates, free fatty acids plus buffering agents and other components |
| INTERACTIVE ® | Surfactant plus Nitrogen Source, Water Conditioning Agent | Surfactants, ammoninated nitrogen salts, polydimethylsiloxane, and polyacrylates |
| JOINT VENTURE ® | Nonionic Surfactant | Proprietary blend of polyalkyleneoxide, modified organosilicones, akylpolyoxylkane ether, and aliphatic ester of c9-c12 fatty acids |
| KINETIC ® | Organo-Silicone Surfactant | Proprietary blend of polyalkyleneoxide modified polydimethylsiloxane and polyoxpropylene-polyoxyethylene block copolymers |
| KINETIC ® HV | Organo-Silicone Surfactant | Proprietary blend of polyalkyleneoxide modified polydimethylsiloxane and polyoxpropylene-polyoxyethylene block copolymers |
| MSO ® | Methylated or Ethylated Vegetable Oil | Proprietary blend of methylated oils and nonionic surfactant |
| ON-LINE ® | Deposition (Drift Control) and/or Retention Agentt, Adjuvant plus Foliar Fertilizer, Water Conditioning Agent | Polyvinyl polymers and foliar nutritionals |
| OPTIMA ® | Buffering Agent or Acidifier | Proprietary blend of polyethoxylated alkyl amines, alkyl polyoxyethylene glycols and organic acids |
| PATROL ® | Surfactant plus Nitrogen Source | NIS plus 28% UAN |
| PENETRATOR ® | Crop Oil (Petroleum) Concentrate, Deposition (Drift Control) and/or Retention Agent | Light range paraffin based petroleum oil and polyol fatty acid esters, and polyethoxylated derivatives |
| PENETRATOR ® PLUS | Crop Oil (Petroleum) Concentrate, Deposition (Drift Control) and/or Retention Agent, Buffering Agent or Acidifier | Mid-range mineral oil, polyol fatty acid esters, polyethoxylated ester thereof, ethoxylated alkyl phosphate esters |
| POINTBLANK ® WM | Deposition (Drift Control) and/or Retention Agent | Proprietary polyvinyl polymer emulsion |
| QUEST ® | Water Conditioning Agent, Nitrogen Source | Proprietary blend of hydroxycarboxylic acid, phosphoric acids, ammonium sulfate, and polyacrylic acid |
| REQUEST ® | Water Conditioning Agent, Nitrogen Source | Proprietary blend of ammonium acrylates, hydroxycarbonoxylates, and sulfates |
| SILWET L-77 ® | Organo-Silicone Surfactant | Polyalkyleneoxide modified heptamethylsiloxane |
| SOY-DEX PLUS ® | Vegetable Oil Concentrate, Deposition (Drift Control) and/or Retention Agent, Buffering Agent or Acidifier | Proprietary blend of vegetable oil, polyol fatty acid ester, polyethoxylated esters thereof, ethoxylated alkylaryl phosphate ester |

TABLE 1-continued

Adjuvants listed by brand name

| Brand Name | Adjuvant type | Main functional components |
|---|---|---|
| STA-PUT PLUS ® | Deposition (Drift Control) and/or Retention Agent | Polyvinyl polymer |
| STRIKE ZONE ® DF | Deposition (Drift Control) and/or Retention Agent | Saccharide and polysaccharide ethers and alkyl polyethoxylated alcohols |
| STRIKE ZONE ® MXD | Deposition (Drift Control) and/or Retention Agent plus Ammonium Sulfate and Water Conditioning Agent | Ammonium and potassium salts and organic polymers |
| TRANSACTIVE ® | Basic Blend, Surfactant plus Nitrogen Source, Buffering Agent or Acidifier | Blend of nonionic surfactant, ammonia salts and buffering agents |
| VEGETABLE OIL CONCENTRATE ® | Vegetable Oil Concentrate, Deposition (Drift Control) and/or Retention Agent | Vegetable oil plus nonionic blend of alkyloxylated alkylphenols and fatty acids (85:15) |
| WIPE OUT ® | Tank Cleaner and/or Neutralizer | Blend of proprietary surfactants |

Further preferred examples of adjuvants are the following substances and compositions:

dioctyl sodium sulphosuccinate, commercially available, for example, in the product series Geropon®;

compositions comprising dioctyl sodium sulphosuccinate and sodium benzoate, commercially available, for example, in the product series Aerosol®; the weight ratio of dioctyl sodium sulphosuccinate:sodium benzoate is preferably from 5:1 to 6: 1;

terminally capped alkoxylated fatty alcohols and terminally capped alkoxylated straight-chain alcohols, commercially available, for example, in the product series Plurafac®; preference is given to ethoxylated and/or butoxylated fatty alcohols and terminally capped ethoxylated and/or butoxylated straight-chain alcohols;

tributylphenol polyglycol ethers having 10 to 15 EO units (where EO means ethylene oxide), commercially available, for example, as Sapogenat®;

polyalkylene oxide-modified polymethylsiloxanes, commercially available, for example, in the product series Silwet®;

branched alkanol alkoxylates of the formula $C_tH_{2t+5}(-CH_2-CH_2-O-)_u-H$, in which t represents numbers from 11 to 13.5 and u represents numbers from 6 to 25 (preferably from 8 to 12) and t and u are average values, commercially available, for example, in the product series Lutensol®;

betaine;

polyalkoxylated triglycerides, where the triglyceride is preferably of vegetable origin, commercially available, for example, in the product series Crovol®;

alkoxylated fatty amines, commercially available, for example, in the product series Armoblen®;

sodium laureth sulphate, commercially available, for example, in the product series Genapol®;

PEG-10 coconut alcohol, commercially available, for example, in the product series Genapol®;

compositions comprising maize syrup, petroleum oil and nonionic emulsifier, commercially available, for example, in the product series Superb®.

Brij® 92, comprising oleyl alcohol ethoxylate with an average of 2 moles of ethoxylate;

Adol® 320, comprising oleyl alcohol;

Priolene® 6910, comprising oleic acid;

Turbocharge®, comprising proprietary blend of oils and short chain ethoxylates;

Merge®, comprising proprietary blend of oils and short chain ethoxylates;

Dash®, comprising proprietary blend of oils and short chain ethoxylates;

Silwet® L77, comprising ethoxylated silicone;

Ethomeen® S12, comprising short chain ethoxylated fatty amine;

Hystrene® 9018, comprising stearic acid.

Suitable surfactants are the alkali metal, alkaline earth metal and ammonium salts of aromatic sulfonic acids, for example of lingo- (Borrespserse® types, Borregaard, Norway), phenol-, naphthalene- (Morwet® types, Akzo Nobel, USA) and dibutylnaphthalenesulfonic acid (Nekal® types, BASF, Germany), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors, and proteins, denatured proteins, polysaccharides (for example methylcellulose), hydrophobe-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone, and their copolymers.

Surfactants which are particularly suitable are anionic, cationic, nonionic and amphoteric surfactants, and polyelectrolytes (wherein nonionic surfactants are preferred). Suitable anionic surfactants are alkali, alkaline earth or ammonium salts of sulfonates, sulfates, phosphates or carboxylates. Examples of sulfonates are alkylarylsulfonates, diphenylsulfonates, alpha-olefin sulfonates, sulfonates of fatty acids and oils, sulfonates of ethoxylated alkylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates.

Suitable nonionic surfactants are block polymers, alkoxylates, N-alkylated fatty acid amides, amine oxides, esters or sugar-based surfactants. Examples of alkoxylates are compounds such as alcohols, alkylphenols, amines, amides, arylphenols, fatty acids or fatty acid esters which have been alkoxylated. Ethylene oxide and/or propylene oxide may be employed for the alkoxylation, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Suitable block polymers are block polymers of the A-B or A-B-A type comprising blocks of polyethylene oxide and polypropylene oxide or of the A-B-C type comprising alkanol, polyethylene oxide and polypropylene oxide. Examples of suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable polyelectrolytes are polyacids or polybases. Examples of polyacids are alkali salts of polyacrylic acid. Examples of polybases are polyvinylamines or polyethyleneamines.

Suitable penetration agents are all customary substances which are capable of improving the penetration of agrochemical substances in plants. The following are preferably suitable: mineral oils, vegetable oils, esters of vegetable oils, fatty acid esters with 10 to 20 carbon atoms in the acid moiety and 1 to 10 carbon atoms in the alcohol moiety, esters of saturated or unsaturated dicarboxylic acids with 4 to 12 carbon atoms in the acid moiety and 1 to 8 carbon atoms in each alcohol moiety, esters of aromatic dicarboxylic acids with 1 to 8 carbon atoms in each alcohol moiety, and furthermore also alkanol alkoxylates. Examples of penetration agents which may be mentioned are:

mineral oils,
rapeseed oil, sunflower oil, corn oil, linseed oil, turnip rape oil, olive oil, cottonseed oil,
rapeseed oil methyl ester, rapeseed oil ethyl ester, turnip rape oil methyl ester, turnip rape oil ethyl ester,
ethylhexyl laurate,
dibutyl succinate, dibutyl adipate, dibutyl phthalate, and alkanol alkoxylates of the formula R—O—(AO)$_m$—R$^1$ in which R represents straight-chain or branched alkyl or alkenyl with 4 to 20 carbon atoms, AO represents C$_2$-C$_4$-alkyleneoxide radical, i.e. an ethylene oxide radical (CH$_2$—CH$_2$—O), a propylene oxide radical (CH(CH$_3$)—CH$_2$—O or CH$_2$—CH(CH$_3$)—O), a butylene oxide radical (CH(C$_2$H$_5$)—CH$_2$—O, C(CH$_3$)$_2$—CH$_2$—O, CH$_2$—C(CH$_3$)$_2$—O or CH$_2$—CH(C$_2$CH$_5$)—O) or mixtures of ethylene oxide and propylene oxide radicals or butylene oxide radicals, m represents numbers from 1 to 30, in particular from 2 to 20 and R$^1$ represents hydrogen or alkyl with 1 to 4 carbon atoms.

In particular embodiments of the invention, the adjuvant comprises at least one nonionic surfactant. For the purpose of being an adjuvant, the nonionic surfactant may be used as such or as a solution in a suitable solvent, e.g. in water or in a non-polar solvent. Suitable non-polar solvents include the aforementioned mineral oils, vegetable oils, esters of vegetable oils, fatty acid esters with 10 to 20 carbon atoms in the acid moiety and 1 to 10 carbon atoms in the alcohol moiety, esters of saturated or unsaturated dicarboxylic acids with 4 to 12 carbon atoms in the acid moiety and 1 to 8 carbon atoms in each alcohol moiety, esters of aromatic dicarboxylic acids with 1 to 8 carbon atoms in the alcohol moiety. The amount of non-ionic surfactants in these solutions may vary from 10 to 80%, in particular from 15 to 50% by weight.

In these particular embodiments of the invention, the adjuvant may contain at least one non-ionic surfactant as the sole surfactant or a combination thereof with one or more anionic or cationic surfactants. In this particular embodiment, the non-ionic surfactant is preferably present in the adjuvant in an amount of at least 50% by weight, based on the total amount of surfactant in the adjuvant.

Amongst the group of non-ionic surfactants, those are preferred which carry at least one poly-C$_2$-C$_4$-alkyleneoxide moiety. A poly-C$_2$-C$_4$-alkyleneoxide moiety is a radical, which has the formula O—(AO)$_k$—R$^x$, where R$^x$ is hydrogen, C$_1$-C$_{20}$-alkyl, C$_1$-C$_{20}$-alkylcarbonyl, or benzyl, in particular hydrogen, C$_1$-C$_4$-alkyl, C$_1$-C$_4$-alkylcarbonyl, k is an integer from 3 to 250, in particular from 3 to 100, especially from 5 to 50 and where AO within the group (AO)k may be identical or different and is selected from ethylene oxide, propylene oxide and butylene oxide, in particular from ethylene oxide and mixtures of ethylene oxide with propyleneoxide. Amongst the group of non-ionic surfactants which carry at least one poly-C$_2$-C$_4$-alkyleneoxide moiety, those are preferred which the poly-C$_2$-C$_4$-alkyleneoxide moiety comprising one or more ethylenoxide moieties and optionally one ore more propylenoxide moieties and/or butyleneoxide moieties.

Suitable non-ionic surfactants which carry at least one poly-C$_2$-C$_4$-alkyleneoxide moiety include, but are not limited to alkoxylates of alcohols, in particular C$_2$-C$_4$-alkoxylates of C$_6$-C$_{22}$-alkanols, alkoxylates of alkylphenols, in particular C$_2$-C$_4$-alkoxylates of C$_6$-C$_{22}$-alkylphenols, alkoxylates of amines, in particular C$_2$-C$_4$-alkoxylates of C$_6$-C$_{22}$-alkylamines, alkoxylates of amides, in particular C$_2$-C$_4$-alkoxylates of C$_6$-C$_{22}$-alkylamides, alkoxylates of arylphenols, in particular C$_2$-C$_4$-alkoxylates of mono-, di- or tristyrylphenol, alkoxylates of fatty acids or fatty acid esters, in particular C$_2$-C$_4$-alkoxylates of C$_6$-C$_{22}$-fatty acids, C$_2$-C$_4$-alkoxylates of C$_6$-C$_{22}$-fatty acid mono or diclycerides and C$_2$-C$_4$-alkoxylates of C$_6$-C$_{22}$-fatty acid sorbitanesters, and block polymers, in particular poly(C$_2$-C$_4$-alkylenoxide) blockcopolymers.

Examples of suitable non-ionic surfactants which carry at least one poly-C$_2$-C$_4$-alkyleneoxide moiety include, but are not limited to:

terminally capped alkoxylated fatty alcohols and terminally capped alkoxylated straight-chain alcohols, commercially available, for example, in the product series Plurafac®; preference is given to ethoxylated and/or butoxylated fatty alcohols and terminally capped ethoxylated and/or butoxylated straight-chain alcohols;

tributylphenol polyglycol ethers having 10 to 15 EO units (where EO means ethylene oxide), commercially available, for example, as Sapogenat®;

polyalkylene oxide-modified polymethylsiloxanes, commercially available, for example, in the product series Silwet®;

branched alkanol alkoxylates of the formula $C_tH_{2t+5}(-CH_2-CH_2-O-)_u-H$, in which t represents numbers from 11 to 13.5 and u represents numbers from 6 to 25 (preferably from 8 to 12) and t and u are average values, commercially available, for example, in the product series Lutensol®;

polyalkoxylated triglycerides, where the triglyceride is preferably of vegetable origin, commercially available, for example, in the product series Crovol®;

alkoxylated fatty amines, commercially available, for example, in the product series Armoblen®;

PEG-10 coconut alcohol, commercially available, for example, in the product series Genapol®;

Brij® 92, comprising oleyl alcohol ethoxylate with an average of 2 moles of ethoxylate;

Turbocharge®, comprising proprietary blend of oils and short chain ethoxylates;

Merge®, comprising proprietary blend of oils and short chain ethoxylates;

Dash®, comprising proprietary blend of oils and short chain ethoxylates;

Silwet® L77, comprising ethoxylated silicone;

Ethomeen® S12, comprising short chain ethoxylated fatty amine;

Alkanol alkoxylates of the formula $R-O-(AO)_m-R^1$ as defined above,

Sylgard® 309 from Dow Corning (3-(3-hydroxypropyl)-heptamethyltrisiloxane, ethoxylated acetate (CAS 125997-17-3) >60%; allyloxy polyethylene glycol monallyl acetate (CAS 27252-87-5), 15-40% polyethylene glycol diacetate 1-5%);

Freeway® (Loveland Products, Inc., Silicone-polyether copolymer, linear alcohol ethoxylates, propylene glycol, dimethylpolysiloxane);

Silwet® L-77 (Helena Chemical Company, polyalkyleneoxide modified heptamethyltrisiloxane (CAS 27306-78-1) 84%, allyloxypolyethyleneglycol methyl ether (CAS 27252-80-8) 16%);

Kinetic® Molecular Zippering Action (Polyalkyleneoxide modified polydimethylsiloxane, Polyoxyethylene-polyoxypropylene copolymer (CAS 9003-11-6), Polyoxypropylene oleate butyl ether (CAS 37281-78-0)).

The non-ionic surfactant which carries at least one poly-$C_2$-$C_4$-alkyleneoxide moiety is preferably selected from polyethoxylated sorbitan fatty acid esters, poly(ethyleneoxide-co-propylenoxide) copolymers, in particular alkyl terminated poly(ethylenoxide-co-propylenoxide) diblock-poylmers or poly(ethyleneoxide-co-propyleneoxide)-triblock polyemrs, and poly-$C_2$-$C_4$-alkyleneoxide modified polydimethylsiloxanes, in particular polyethyleneoxide modified polydimethyldisiloxanes, as well as mixtures thereof.

In this particular preferred embodiment of the invention, the non-ionic surfactant which carries at least one poly-$C_2$-$C_4$-alkyleneoxide moiety may be the sole non-ionic surfactant of the adjuvant or the adjuvant contains a combination thereof with one or more non-ionic surfactants. In this particular embodiment, the non-ionic surfactant which carries at least one poly-$C_2$-$C_4$-alkyleneoxide moiety is preferably present in the adjuvant in an amount of at least 50% by weight, based on the total amount of surfactant in the adjuvant.

In a particular embodiments of the invention, the adjuvant comprises at least one silicone-based adjuvant. For the purpose of being an adjuvant, the silicone-based adjuvant may be used as such or as a combination thereof with one or more other adjuvants, in particular with one or more non-ionic surfactants.

Typical silicone based adjuvants contain at least one non-ionic polydi-$C_1$-$C_4$-alkylsiloxane, in particular at least one polydimethylsiloxane having at least one oligo- or polydi-$C_1$-$C_4$-alkylsiloxane moiety, in particular at least one oligo- or polydimethylsiloxane moiety. A polydi-$C_1$-$C_4$-alkylsiloxane moiety is a radical made of repeating units of the formula

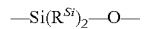

where $R^{Si}$ is $C_1$-$C_4$-alkyl, in particular methyl (=polydimethylsiloxane). The oligo- or polydi-$C_1$-$C_4$-alkylsiloxane moiety may be cyclic or acyclic. The oligo- or polydi-$C_1$-$C_4$-alkylsiloxane moiety will generally have at least 3 silicon atoms, e.g. from 3 to 100 Si atoms (number average). The oligo- or polydi-$C_1$-$C_4$-alkylsiloxane, in particular the polydimethylsiloxane moiety may have non-ionic terminal groups different from methyl, e.g. OH or longer chain alkyl, (e.g. $C_2$-$C_{10}$-alkyl) or $C_2$-$C_{10}$-alkyl substituted by 1 or 2 OH radicals.

In addition to the at least one oligo- or polydi-$C_1$-$C_4$-alkylsiloxane moiety, the non-ionic polydi-$C_1$-$C_4$-alkylsiloxane may have one or more polar groups, in particular one or more non-ionic polar groups. Suitable non-ionic polar groups include but are not limited to alkyl and cycloalkyl radicals having two or more, e.g. 2, 3, 4, or 5 hydroxy groups, mono- or oligosaccharid radicals and poly-$C_2$-$C_4$-alkyleneoxide moieties, in particular polyethylenoxide moieties.

In a particular preferred embodiment the silicone-based adjuvant comprises a poly-$C_2$-$C_4$-alkyleneoxide modified polydi-$C_1$-$C_4$-alkylsiloxane, in particular a poly-$C_2$-$C_4$-alkyleneoxide modified polydimethylsiloxane, especially a polyethylene oxide modified polydimethylsiloxane. In the poly-$C_2$-$C_4$-alkyleneoxide modified polydi-$C_1$-$C_4$-alkylsiloxanes, the poly-$C_2$-$C_4$-alkyleneoxide moieties, in particular polyethylenoxide moieties will usually have from 5 to 200 in particular from 10 to 100 $C_2$-$C_4$-alkyleneoxide repeating units, in particular from 5 to 200 and especially from 10 to 100 ethylenoxide repeating units.

In this particular embodiment, the silicone based adjuvant is preferably present in the adjuvant in an amount of at least 30% by weight, based on the total amount of adjuvant.

Examples of silicone-based adjuvants are:

Sylgard® 309 from Dow Corning (3-(3-hydroxypropyl)-heptamethyltrisiloxane, ethoxylated acetate (CAS 125997-17-3) >60%; allyloxy polyethylene glycol monallyl acetate (CAS 27252-87-5), 15-40% polyethylene glycol diacetate 1-5%);

Freeway® (Loveland Products, Inc., Silicone-polyether copolymer, linear alcohol ethoxylates, propylene glycol, dimethylpolysiloxane);

Silwet® L-77 (Helena Chemical Company, polyalkyleneoxide modified heptamethyltrisiloxane (CAS 27306-78-1) 84%, allyloxypolyethyleneglycol methyl ether (CAS 27252-80-8) 16%);

Kinetic® Molecular Zippering Action (Polyalkyleneoxide modified polydimethylsiloxane, Polyoxyethylene-polyoxypropylene copolymer (CAS 9003-11-6), Polyoxypropylene oleate butyl ether (CAS 37281-78-0)).

In a further especially preferred embodiment, the adjuvant comprises polyalkyleneoxide modified polydimethylsiloxane and poly(ethylene oxide-block-propylene oxide). Examples are commercially available, such as Kinetic® Molecular Zippering Action from Helena.

In a further particular embodiments of the invention, the adjuvant comprises at least one crop oil concentrate. For the purpose of being an adjuvant, the crop oil concentrate may be used as such or as a combination thereof with one or more other adjuvants, in particular with one or more non-ionic surfactants.

Crop oil concentrates are usually a mixture comprising a non-polar high boiling organic liquid and at least one surfactant, in particular at least one non-ionic surfactant or a mixture of at least one non-ionic surfactant and at least one anionic surfactant. Suitable non-polar high boiling organic liquids for crop-oil concentrates include hydrocarbon solvents, in particular a non-aromatic hydrocarbon solvent, such as aliphatic mineral oils, aliphatic petroleum oils, white oils and light and heavy paraffinic oils, and fatty acid triglycerides, e.g. vegetable oils. In particular embodiments the crop oil concentrate contains at least one hydrocarbon solvent, a non-aromatic hydrocarbon solvent and at least one non-ionic surfactant. In particular embodiments of the crop-oil concentrates, the non-ionic surfactant is selected from polyol fatty acid esters, polyoxyethylated polyol fatty acid esters, alkylphenol ethoxylates and fatty acids and mixtures thereof. In especially preferred embodiments of the crop-oil concentrates, the non-ionic surfactant is selected from sorbitan fatty acid esters such as sorbitan mono- or dilaurat or sorbitan mono- or dioleate, polyoxyethylated sorbitan fatty acid esters such as polyethoxylated sorbitan mono- or dilaurat or polyethoxylated sorbitan mono- or dioleate, and mixtures thereof.

Examples of suitable crop oil concentrates are:
Agri-dex® (Helena Chemical Co.), a mixture of heavy and light range paraffin base petroleum oils (CAS 64741-88-4, 64741-89-5) 82%, polyol fatty acid esters and polyoxyethylated polyol fatty acid esters 17%);
Red-Top Mor-Act® Adjuvant (Wilbur-Ellis Co., Non-phytotoxic paraffin base petroleum oil 83%, CAS 8012-95-1, Polyol fatty acid esters and polyethoxylated derivatives thereof 15%);
Herbimax® Petroleum Oil-Surfactant Adjuvant (Loveland Products, Inc., Petroleum hydrocarbons 83% (CAS 64741-50-0), odorless aliphatic petroleum solvent (CAS 64742-89-8), Alkylphenol ethoxylate, tall oil fatty acid)

In an especially preferred embodiment, the adjuvant comprises petroleum oil and surfactant, such as a sorbitan fatty acid ester and a polyethoxylated sorbitan fatty acid ester. More preferably, the adjuvant (crop-oil concentrate) comprises at least 50 wt %, e.g. from 50 to 99 wt % or from 60 to 95 wt %, based on the total weight of the adjuvant, of petroleum oil and up to 50 wt %, e.g. from 1 to 50 wt % or from 5 to 40 wt %, based on the total weight of the adjuvant, of the at least one surfactant. Examples are commercially available, such as Agridex® from Bayer Crop Science.

In a further embodiment of the invention, the composition in addition to the compound of formulae I or II comprises at least one alkoxylated aliphatic alcohol, hereinafter also termed as alkoxylate. The aliphatic alcohol, on which the alkoxylated aliphatic alcohol is based, may be linear or branched. The aliphatic alcohol, on which the alkoxylated aliphatic alcohol is based, may have 5 to 36 carbon atoms, preferably it has 10 to 32 carbon atoms, more preferably 14 to 26 carbon atoms, and in particular 15 to 20 carbon atoms. It is also possible to use a mixture of alcoxylated aliphatic alcohols with different numbers of carbon atoms in the aliphatic radical of the aliphatic alcohol, on which the alkoxylated aliphatic alcohol is based. The aliphatic alcohol, on which the alkoxylated aliphatic alcohol is based, is preferably a linear aliphatic alcohol, and in particular a linear aliphatic alcohol with 14 to 22 carbon atoms or with 16 to 20 carbon atoms.

Alkoxylated in context with alkoxylated aliphatic alcohol means that the OH moiety of the aliphatic alcohol has been replaced by a polyoxyalkylene or polyalkyleneoxide moiety, which are synonyms. Polyoxyalkylene, in terms of the present invention, is an aliphatic polyether radical which build from alkylenoxide repeating units A-O, where A is alkandiyl, in particular $C_2$-$C_5$-alkandiyl. Polyoxyalkylene, in terms of the present invention, is preferably a poly-$C_2$-$C_5$-alkyleneoxide moiety, more preferably a poly-$C_2$-$C_4$-alkyleneoxide moiety, especially a poly-$C_2$-$C_3$-alkyleneoxide moiety, e.g. a polyethylenoxide moiety, a polypropylenoxide moiety, a poly(ethylenoxide-co-propylenoxide) moiety, a poly(ethylenoxide-co-butylenoxide) moiety or a poly(ethylenoxide-co-pentylenoxide) moiety. The number of alkyleneoxide repeating units in the polyoxyalkylene radical is generally from 1 to 100 or from 2 to 100, preferably from 5 to 40, more preferably from 10 to 30 and in particular from 12 to 20

In a preferred embodiment the alkoxylated aliphatic alcohol (alkoxylate) is selected from alkoxylated alcohols of the formula (A)

$$R^a\text{—O—}(C_mH_{2m}O)_x\text{—}(C_nH_{2n}O)_y\text{—}(C_pH_{2p}O)_z\text{—}R^b \quad (A)$$

in which
$R^a$ represents $C_5$-$C_{36}$-alkyl, $C_5$-$C_{36}$-alkenyl or mixture thereof, preferably linear $C_5$-$C_{36}$-alkyl, $C_5$-$C_{36}$-alkenyl, or a mixture thereof, in particular linear $C_{14}$-$C_{36}$-alkyl, $C_{14}$-$C_{36}$-alkenyl, or mixture thereof, or linear $C_{14}$-$C_{26}$-alkyl, $C_{14}$-$C_{26}$-alkenyl, or mixture thereof, more preferably linear $C_{14}$-$C_{22}$-alkyl, or mixture thereof, especially linear $C_{16}$-$C_{20}$-alkyl, or mixture thereof;
$R^b$ represents H or $C_1$-$C_{12}$-alkyl, in particular H or $C_1$-$C_4$-alkyl, preferably H or methyl, especially H;
m, n, p represent, independently of one another, an integer from 2 to 16, preferably from 2 to 5, more preferably 2, 3 or 2 and 3 (in particular 2 and 3);
x, y, z represent, independently of one another, a number from 0 to 100, preferably a number from 0 to 30, more preferably from 0 to 20; and
x+y+z corresponds to a value from 1 to 100, preferably from 5 to 40, more preferably from 10 to 30 and in particular from 12 to 20.

$R^a$ may be linear or branched, preferably it is linear. $R^a$ may be saturated or unsaturated, preferably it is saturated. $R^a$ may be substituted or unsubstituted, preferably it is unsubstituted. Preferably, $R^a$ represents linear $C_5$-$C_{36}$-alkyl, $C_5$-$C_{36}$-alkenyl, or a mixture thereof. In particular, $R^a$ represents linear $C_{14}$-$C_{36}$-alkyl, $C_{14}$-$C_{36}$-alkenyl, or mixture thereof, in particular linear $C_{14}$-$C_{26}$-alkyl, $C_{14}$-$C_{26}$-alkenyl, or mixture thereof. More preferably, $R^a$ represents a linear $C_{14}$-$C_{22}$-alkyl, or mixture thereof. Especially preferred, $R^a$ represents a linear $C_{16}$-$C_{20}$-alkyl, or mixture thereof.

$R^b$ represents preferably H or methyl, in particular H.

Preferably, m, n, p represent, independently of one another, an integer from 2 to 5, more preferably 2, 3 or 2 and 3 (in particular 2 and 3).

Preferably, x, y, z represent, independently of one another, a number from 0 to 30, more preferably from 0 to 20. Preferably, x+y+z corresponds to a value from 5 to 40, more preferably from 10 to 30 and in particular from 12 to 20.

According to a particular embodiment, alcohol alkoxylates of the formula (A) are used in which m=2 and the value of x is greater than zero. This relates on this occasion to alcohol alkoxylates of EO type to which belong especially alcohol ethoxylates (m=2; x>zero; y, z=zero) and alcohol alkoxylates with an EO block bonded to the alcohol portion (m=2; x>zero; y and/or z>zero). Mention may be made, from the alcohol alkoxylates with an EO block bonded to the alcohol portion, especially of EO-PO block alkoxylates (m=2; x>zero; y>zero; n=3; z=0), EO-PeO block alkoxylates (m=2; x>zero; y>zero; n=5; z=0) and EO-PO-EO block alkoxylates (m, p=2; x, z>zero; y>zero; n=3). In particular preferred are EO-PO block alkoxylates (m=2; x>zero; y>zero; n=3; z=0).

Here and in the following EO represents $CH_2CH_2O$. PO represents $CH(CH_3)CH_2O$ or $CH_2CH(CH_3)O$. BuO represents $CH(C_2H_5)CH_2O$, $C(CH_3)_2CH_2O$, $CH_2C(CH_3)_2O$, $CH(CH_3)CH(CH_3)O$ or $CH_2CH(C_2H_5)O$ and PeO represents $(C_5H_{10}O)$.

Preference is given to EO-PO block alkoxylates in which the ratio of EO to PO (x to y) is 10:1 to 1:10, preferably 1:1 to 1:12 and in particular 1:2 to 1:8. In this context, the degree of ethoxylation (value of x) is generally 1 to 20, preferably 2 to 15 and in particular 2 to 10 and the degree of propoxylation (value of y) is generally 1 to 30, preferably 4 to 20 and in particular 8 to 16. The overall degree of alkoxylation, i.e. the sum of EO and PO units, is generally 2 to 50, preferably 4 to 30 and in particular 6 to 20. Preference is furthermore given to EO-PO block alkoxylates in which the ratio of EO to PeO (x to y) is 2:1 to 25:1 and in particular 4:1 to 15:1. In this context, the degree of ethoxylation (value of x) is generally 1 to 50, preferably 4 to 25 and in particular 6 to 15 and the degree of pentoxylation (value of y) is generally 0.5 to 20, preferably 0.5 to 4 and in particular 0.5 to 2. The overall degree of alkoxylation, i.e. the sum of EO and PeO units, is generally 1.5 to 70, preferably 4.5 to 29 and in particular 6.5 to 17.

According to a further particular embodiment, alcohol alkoxylates of the formula (A) are used in which n =2, the values of x and y are both greater than zero and z =0. On this occasion also, these are alcohol alkoxylates of EO type but in which the EO block is terminally bonded. These include especially PO-EO block alkoxylates (n=2; x>zero; y>zero; m=3; z=0) and PeO-EO block alkoxylates (n=2; x>zero; y>zero; m=5; z=0).

Preference is given to PO-EO block alkoxylates in which the ratio of PO to EO (x to y) is 1:10 to 10:1, preferably 12:1 to 1:1 and in particular 2:1 to 8:1. In this context, the degree of ethoxylation (value of y) is generally 1 to 20, preferably 2 to 15 and in particular 2 to 10. The degree of propoxylation (value of x) is generally 0.5 to 30, preferably 4 to 20 and in particular 6 to 16. The overall degree of alkoxylation, i.e. the sum of EO and PO units, is generally 1.5 to 50, preferably 2.5 to 30 and in particular 8 to 20.

Preference is furthermore given to PeO-EO block alkoxylates in which the ratio of PeO to EO (x to y) is 1:50 to 1:3 and in particular 1:25 to 1:5. In this context, the degree of pentoxylation (value of x) is generally 0.5 to 20, preferably 0.5 to 4 and in particular 0.5 to 2 and the degree of ethoxylation (value of y) is generally 3 to 50, preferably 4 to 25 and in particular 5 to 15. The overall degree of alkoxylation, i.e. the sum of EO and PeO units, is generally 3.5 to 70, preferably 4.5 to 45 and in particular 5.5 to 17.

According to a further particular embodiment, alcohol alkoxylates of the formula (A) are used in which the values of x, y and z are all greater than zero. These include especially PeO-EO-PO block alkoxylates (m=5; x>zero; n=2; y>zero; m=3; z>zero).

In an especially preferred embodiment the alkoxlyate is selected from alkoxylated alcohols of the formula (A), in which $R^a$ represents linear $C_{12}$-$C_{22}$-alkyl, especially linear$C_{10}$-$C_{20}$ alkyl or a mixture thereof;

$R^b$ represents H or $C_1$-$C_4$-alkyl, preferably H or methyl, in particular H;

m,n,p represent, independently of one another, an integer from 2 to 5, preferably from 2 to 3;

x, y, z represent, independently of one another, a number from 0 to 50; and x+y+z corresponds to a value from 5 to 50, preferably from 8 to 25.

The wetting power by immersion of the alkoxlyate is usually at least 120 seconds, preferably at least 180 s, especially at least 220 s. The wetting power is usually analyzed according to DIN 1772 at room temperature at 1 g/L in 2 g/l sodium carbonate.

The surface tension of the alkoxylate is usually at least 30 mN/m, preferably at least 31 mN/m, and in particular at least 32 mN/m. Further on, the surface tension is preferably from 30 to 40 mN/m, and in particular from 30 to 35 mN/m. The surface tension may be analyzed according to DIN 14370 at room temperature at 1 g/L.

Preferably, the alkoxylate has a wetting power by immersion of at least 120 s and a surface tension of at least 30 mN/m. More preferably, the alkoxylate has a wetting power by immersion of at least 180 s and a surface tension from 30 to 40 mN/m.

Alkoxylates are known and may be prepared by known methods, such as WO 98/35553, WO 00/35278 or EP 0 681 865. Many alkoxlyates are commercially available, for example Atplus® 242, Atplus® 245, Atplus® MBA 1303 from Croda, Plurafac® LF types from BASF SE, Agnique® BP 24-24, Agnique® BP 24-36, Agnique® BP 24-45, Agnique® BP 24-54, Agnique® BP24-52R from Cognis.

The preferred compositions according to the invention (preferably in form of an emulsion concentrate) comprises usually at least 10 wt % of the alkoxylate, e.g. form 10 to 70 wt %, preferably at least 15 wt %, and in particular from 15 to 50 wt % based on the composition.

In the preferred composition according to the invention the alkoxylated aliphatic alcohol (alkoxylate) or the mixture of different alkoxylated alcohols may be the sole adjuvant. However, it is also preferred, if the alkoxylated aliphatic alcohol, in particular the alkoxylated aliphatic alcohol of formula A is combined with a different adjuvant. In the preferred compositions according to the invention (preferably in form of an emulsion concentrate), which comprise at least one alkoxylated aliphatic alcohol and at least one adjuvant different therefrom, the total amount of adjuvant is generally at least 10 wt %, e.g. form 10 to 70 wt %, preferably at least 15 wt %, and in particular from 15 to 50 wt %, based on the composition.

In the preferred compositions according to the invention (e.g. in form of an emulsion concentrate or a tank mix), which comprise at least one alkoxylated aliphatic alcohol and at least one adjuvant different therefrom, the weight ratio of the alkoxylated aliphatic alcohol(s) and the at least one adjuvant different therefrom will generally be from 1:10 to 10:1, in particular from 5:1 to 1:5 or from 3:1 to 1:3.

The inventive composition may also comprise auxiliaries which are customary in agrochemical formulations. The auxiliaries used depend on the particular application form and active substance, respectively. Examples for suitable auxiliaries are solvents, solid carriers, dispersants or emulsifiers (such as further solubilizers, protective colloids, surfactants and adhesion agents), organic and inorganic thickeners, bactericides, anti-freezing agents, anti-foaming agents, if appropriate colorants and tackifiers or binders (e. g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e. g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e. g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (wetters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany),and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokalan® types, BASF, Germany), polyalkoxylates, polyvinylamines (Lupasol® types, BASF, Germany), polyvinylpyrrolidone and the copolymers therof.

Examples for thickeners (i. e. compounds that impart a modified flowability to formulations, i. e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides may be added for preservation and stabilization of the formulation. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof. Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds the respective active compounds present in the inventive compositions and, if appropriate, further active substances, with at least one solid carrier. Granules, e. g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

Examples for formulation types are:
1. Composition Types for Dilution with Water
i) Water-Soluble Concentrates (SL, LS)

10 parts by weight of active substance (e.g. Insecticide A) is dissolved in 90 parts by weight of water or in a water-soluble solvent. As an alternative, wetting agents or other auxiliaries are added. The active substance dissolves upon dilution with water. In this way, a formulation having a content of 10% by weight of active substance is obtained.
ii) Dispersible Concentrates (DC)

20 parts by weight of active substance (e.g. Insecticide A) is dissolved in 70 parts by weight of cyclohexanone with addition of 10 parts by weight of a dispersant, e. g. polyvinylpyrrolidone. Dilution with water gives a dispersion. The active substance content is 20% by weight.
iii) Emulsifiable Concentrates (EC)

15 parts by weight of active substance (e.g. Insecticide A) is dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.
iv) Emulsions (EW, EO, ES)

25 parts by weight of active substance (e.g. Insecticide A) is dissolved in 35 parts by weight of xylene with addition of calcium dodecylbenzenesulfonate and castor oil ethoxylate (in each case 5 parts by weight). This composition is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of active substance (e.g. Insecticide A) is comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of active substance (e.g. Insecticide A) is ground finely with addition of 50 parts by weight of dispersants and wetting agents and prepared as water-dispersible or water-soluble granules by means of technical appliances (e. g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of active substance (e.g. Insecticide A) is ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight active substance (e.g. Insecticide A) is comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of active substance (e.g. Insecticide A) is ground finely and mixed intimately with 95 parts by weight of finely divided kaolin. This gives a dustable composition having an active substance content of 5% by weight.

x) Granules (GR, FG, GG, MG)

0.5 parts by weight of active substance (e.g. Insecticide A) is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of active substance (e.g. Insecticide A) is dissolved in 90 parts by weight of an organic solvent, e. g. xylene. This gives a composition to be applied undiluted having an active substance content of 10% by weight.

The agrochemical formulations generally comprise between 0.01 and 95%, preferably between 0.1 and 90%, most preferably between 0.5 and 90%, by weight of active substances. The Insecticide A is employed in a purity of from 90% to 100%, preferably from 95% to 100% (according to NMR spectrum).

The inventive composition can be used as such or in the form of their agrochemical formulations, e. g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the compounds present in the inventive compositions.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of compounds of the inventive compositions.

The compounds of the inventive compositions may also be used successfully in the ultra-low-volume process (ULV), it being possible to apply compositions comprising over 95% by weight of active substance, or even to apply the active substance without additives.

Various types of oils, wetters, adjuvants, herbicides, fungicides, other pesticides, or bactericides may be added to the active compounds, if appropriate not until immediately prior to use (tank mix). These agents can be admixed with the compounds of the inventive composition in a weight ratio of 1:100 to 100:1, preferably 1:10 to 10:1.

Compositions of this invention may also contain fertilizers such as ammonium nitrate, urea, potash, and superphosphate, phytotoxicants and plant growth regulators and safeners. These may be used sequentially or in combination with the above-described compositions, if appropriate also added only immediately prior to use (tank mix). For example, the plant(s) may be sprayed with a composition of this invention either before or after being treated with the fertilizers.

The compounds of the inventive composition can be used individually or already partially or completely mixed with one another to prepare the composition according to the invention. It is also possible for them to be packaged and used further as combination composition such as a kit of parts. In one embodiment of the invention, a kit of parts comprises, as separate components, a) the pesticide, and b) the adjuvant, for combined use. The kits may include one or more, including all, components that may be used to prepare a subject agrochemical composition. In those embodiments where more than two components are provided in a kit, the components may already be combined together and as such are packaged in a single container such as a vial, bottle, can, pouch, bag or canister. In other embodiments, two or more components of a kit may be packaged separately, i. e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

The present invention further relates to a method for protecting plants from attack or infestation by insects, acarids or nematodes comprising contacting the plant, or the soil or water in which the plant is growing, with the inventive composition in pesticidally effective amounts.

The present invention further relates to a method for controlling insects, arachnids or nematodes comprising contacting an insect, acarid or nematode or their food supply, habitat, breeding grounds or their locus with the inventive composition in pesticidally effective amounts.

The inventive composition exhibits outstanding action against animal pests (e.g. insects, acarids or nematodes) from the following orders:

insects from the order of the lepidopterans (*Lepidoptera*), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (*Coleoptera*), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga sp., Phyllopertha horticola, Phyllotreta nemorum, Phyllotreta striolata, Popillia japonica, Sitona lineatus* and *Sitophilus granaria*, flies, mosquitoes (*Diptera*), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates spp., Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga sp., Simulium vittatum, Stomoxys calcitrans, Tabanus bovinus, Tabanus atratus, Tabanus lineola,* and *Tabanus similis, Tipula oleracea,* and *Tipula paludosa* thrips (*Thysanoptera*), e.g. *Dichromothrips corbetti, Dichromothrips ssp, Frankliniella fusca, Frankliniella occidentalis, Frankliniella tritici, Scirtothrips citri, Thrips oryzae, Thrips palmi* and *Thrips tabaci*, termites (*Isoptera*), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus*, cockroaches (*Blattaria-Blattodea*), e.g. *Blattella germanica, Blattella asahinae, Periplaneta americana, Periplaneta japonica, Periplaneta brunnea, Periplaneta fuligginosa, Periplaneta australasiae,* and *Blatta orientalis*, true bugs (*Hemiptera*), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis , Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus*

*ascalonicus, Myzus cerasi, Myzus varians, Nasonovia ribisnigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma spp.,* and *Arilus critatus.* ants, bees, wasps, sawflies (*Hymenoptera*), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile,* crickets, grasshoppers, locusts (*Orthoptera*), e.g. *Acheta domestica, Gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina,*

*Arachnoidea,* such as arachnids (*Acarina*), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis; Araneida,* e.g. *Latrodectus mactans,* and *Loxosceles reclusa,* fleas (*Siphonaptera*), e.g. *Ctenocephalides felis, Ctenocephalides canis, Xenopsylla cheopis, Pulex irritans, Tunga penetrans,* and *Nosopsyllus fasciatus,* silverfish, firebrat (*Thysanura*), e.g. *Lepisma saccharina* and *Thermobia domestica,* centipedes (*Chilopoda*), e.g. *Scutigera coleoptrata,* millipedes (*Diplopoda*), e.g. *Narceus* spp.,

Earwigs (*Dermaptera*), e.g. *forficula auricularia,* lice (*Phthiraptera*), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus,* plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolii,* and other *Heterodera* species; seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenchus* species; ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species; sheath nematodes, *Hemicycliophora* species and *Hemicriconemoides* species; *Hirshmanniella* species; lance nematodes, *Hoplolaimus columbus, Hoplolaimus galeatus* and other *Hoplolaimus* species; false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scribneri, Pratylenchus vulnus, Pratylenchus zeae* and other *Pratylenchus* species; *Radinaphelenchus cocophilus* and other *Radinaphelenchus* species; burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species; stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudatum* and other *Xiphinema* species; and other plant parasitic nematode species.

The composition according to the invention can be applied to any and all developmental stages of pests, such as egg, larva, pupa, and adult. The pests may be controlled by contacting the target pest, its food supply, habitat, breeding ground or its locus with a pesticidally effective amount of the inventive compositions. "Locus" means a plant, plant propagation material (preferably seed), soil, area, material or environment in which a pest is growing or may grow.

In general, "pesticidally effective amount" means the amount of the inventive compositions needed to achieve an observable effect on growth, including the effects of necrosis, death, retardation, prevention, and removal, destruction, or otherwise diminishing the occurrence and activity of the animal pest. The pesticidally effective amount can vary for the various compositions used in the invention. A pesticidally effective amount of the compositions will also vary according to the prevailing conditions such as desired pesticidal effect and duration, weather, target species, locus, mode of application, and the like.

The inventive compositions are employed by treating the animal pest on the plants, plant propagation materials (preferably seeds), materials or soil to be protected from pesticidal attack with a pesticidally effective amount of the active compounds. The application can be carried out both before and after the infection of the materials, plants or plant propagation materials (preferably seeds) by the pests.

Peferably, the inventive compositions are employed by treating the animal pests or the plants or soil to be protected from pesticidal attack via foliar application with a pesticidally effective amount of the active compounds. Also herein, the application can be carried out both before and after the infection of the plants by the pests.

In the method of combating animal pests (insects, acarids or nematodes) depending on the type of compound and the desired effect, the application rates of the compositions according to the invention are from 0,1 g/ha to 10000 g/ha, preferably 1 g/ha to 5000 g/ha, more preferably from 20 to 1000 g/ha, most preferably from 10 to 750 g/ha, in particular from 20 to 500 g/ha.

In the context of the present invention, the term plant refers to an entire plant, a part of the plant or the propagation material of the plant.

Plants and as well as the propagation material of said plants, which can be treated with the inventive compositions include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, compositions according to the present invention can be applied (as seed treatment, spray treatment, in furrow or by any other means) also to plants which have been modified by breeding, mutagenesis or genetic engineering including but not limiting to agricultural biotech products on the market or in development (cf. http://www-.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted posttranstional modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e.g. EP-A 242 236, EP-A 242 246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as 5-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The inventive composition are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non phytophathogenic pests such as ants, termites, wasps, flies, mosquitoes, crickets, locusts, or cockroaches the inventive composition are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by non-phytopathogenic insects (e.g. malaria, dengue and yellow fever, lymphatic filariasis, and leishmaniasis) with the inventive compositions and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a composition including the inventive compositions, optionally a repellent and at least one binder.

The inventive compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the composition of the active ingredients is from 0.001 to 80 weights %, preferably from 0.01 to 50 weight % and most preferably from 0.01 to 15 weight %.

The invention further relates to a method for protection of plant propagation material comprising contacting the plant propagation material with a composition according to the invention in pesticidally effective amounts.

As mentioned at the outset, in a preferred embodiment of the invention, the inventive compositions are used for the protection of the seed and the seedlings' roots and shoots, preferably the seeds.

Seed treatment can be made into the seedbox before planting into the field.

For seed treatment purposes, the weight ration in the inventive composition generally depends from the properties of the compounds of the inventive compositions.

Customary formulations, which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)

G Water-dispersible powders and water-soluble powders (WP, SP, WS)
H Gel-Formulations (GF)
I Dustable powders (DP, DS)

These compositions can be applied to plant propagation materials, particularly seeds, diluted or undiluted. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying the inventive composition and compositions thereof, respectively, on to plant propagation material, especially seeds, are known in the art, and include but not limited to, seed dressing, seed coating, seed dusting, seed soaking, seed film coating, seed multilayer coating, seed encrusting, seed dripping, and seed pelleting.

In a preferred embodiment, the compounds or the compositions thereof, respectively, are applied on to the plant propagation material by a method such that germination is not induced, e. g. by seed dressing, pelleting, coating and dusting.

In the treatment of plant propagation material (preferably seed), the application rates of the inventive composition are generally for the formulated product (which usually comprises from 10 to 750 g/l of the active(s)).

The invention also relates to the propagation products of plants, and especially the seed comprising, that is, coated with and/or containing, an inventive composition as defined above. The plant propagation material (preferably seed) comprises the inventive compositions in an amount of from 0.1 g to 10 kg per 100 kg of plant propagation material (preferably seed), preferably 0.1 g to 1 kg per 100 kg of plant propagation material (preferably seed).

The separate or joint application of the compounds of the inventive compositions is carried out by spraying or dusting the seeds, the seedlings, the plants or the soils before or after sowing of the plants or before or after emergence of the plants.

In accordance with one variant of soil application, a further subject of the invention is in furrow treatment, which comprises adding a solid or liquid formulation comprising the inventive compositions to the open furrow, in which seeds have been sown or, alternatively, applying seeds and formulation simultaneously to the open furrow.

In an especially preferred embodiment, the composition according to the invention is a emulsion concentrate (also termed emulsifiable concentrate or EC). The emulsion concentrate generally comprises at least 10 wt %, e.g. 10 to 70 wt %, based on the weight of the emulsion concentrate, of the adjuvant. Preferably the EC comprises 0.5 to 30 wt % of Insecticide A, 10 to 70 wt % of adjuvant, and formulation auxiliaries up to 100%, the formulation auxiliaries comprising in particular at least one organic solvent, preferably in amounts from 20 to 70 wt %, wherein all components sum up to 100 wt %.

In particular, the EC comprises 1 to 15 wt % of Insecticide A, 15 to 60 wt % of adjuvant, 25 to 60 wt % of organic solvent, and optionally further formulation auxiliaries up to 100%, wherein all components sum up to 100 wt %.

In likewise preferred embodiments, the EC comprises 0.5 to 30 wt % of Insecticide B, 10 to 70 wt % of adjuvant, and formulation auxiliaries up to 100%, the formulation auxiliaries comprising in particular at least one organic solvent, preferably in amounts from 20 to 70 wt %, wherein all components sum up to 100 wt %. In particular, the EC comprises 1 to 15 wt % of Insecticide B, 15 to 60 wt % of adjuvant, 25 to 60 wt % of organic solvent, and optionally further formulation auxiliaries up to 100%, wherein all components sum up to 100 wt %.

The present invention further relates to a method for preparing the inventive composition comprising contacting the pesticide and the adjuvant. Usually, the contacting takes place when preparing an agrochemical formulation by known means. The contacting of the components may be achieved by conventional equipment at any temperature, such as room temperature. Preferred mixing methods are those which are applied to prepare agrochemical compositions.

The present invention further relates to a method for preparing an aqueous tank-mix comprises the steps of
a) providing a composition containing the pesticide;
b) providing a composition containing the adjuvant; and
c) contacting the compositions of steps a) and b).

Preferably, the composition of step a) is an emulsion concentrate (EC), suspension concentrate (SC), or a mini-emulsion (ME). In particular, the composition of step a) is an aqueous SC, which comprises the pesticide in suspended form.

In another particular embodiment, the composition of step a) is an aqueous ME, which comprises the pesticide in emulsified form. Preferably, the tank-mix contains 0.01 to 5 wt % of the adjuvant.

In a preferred embodiment, the method for preparing an aqueous tank-mix comprises the steps of
a) providing an EC, SC or ME composition containing the pesticide;
b) providing a composition containing the adjuvant; and
c) contacting the compositions of steps a) and b),
wherein the adjuvant is a silicone-based adjuvant or a crop oil concentrate.

The present invention further relates to a use of the adjuvant for increasing the efficacy of the pesticide.

Advantages of the present invention are for example, that the composition according to the invention has increased insecticidal efficacy, and that the efficacy is prolonged.

In an especially preferred embodiment, the composition according to the invention is a emulsion concentrate (EC), which comprises at least one alkoxylated aliphatic alcohol as defined above. The amount of alkoxylated aliphatic alcohol will be generally at least 10 wt %, based on the weight of the emulsion concentrate. Preferably the EC comprises 0.5 to 30 wt % of Insecticide A, 10 to 70 wt % of alkoxylated aliphatic alcohol, in particular the alcohol of the formula (A), and formulation auxiliaries up to 100%, the formulation auxiliaries comprising in particular at least one organic solvent, preferably in amounts from 20 to 70 wt %, wherein all components sum up to 100 wt %.

In particular, the EC comprises 1 to 15 wt % of Insecticide A, 15 to 60 wt % of alkoxylated alcohol of the formula (A), wherein $R^a$ in particular represents linear $C_{12}$-$C_{22}$-alkyl, or a mixture thereof, Rb in particular represents H or $C_1$-$C_4$-alkyl (more preferably H), m, n, p preferably represent, independently of one another, an integer from 2 to 5 (more preferably from 2 to 3), x, y, z preferably represent, independently of one another, a number from 0 to 50, and x +y +z preferably corresponds to a value from 5 to 50, more preferably from 8 to 25), 25 to 60 wt % of organic solvent, and further formulation auxiliaries up to 100%, wherein all components sum up to 100 wt %.

Likewise preferably, the EC comprises 0.5 to 30 wt % of Insecticide A, 10 to 70 wt % of alkoxylated aliphatic alcohol, in particular the alcohol of the formula (A), and formulation auxiliaries up to 100%, the formulation auxiliaries comprising in particular at least one organic solvent, preferably in amounts from 20 to 70 wt %, wherein all components sum up to 100 wt %. In particular the EC comprises 1 to 15 wt % of Insecticide B, 15 to 60 wt % of alkoxylated alcohol of the formula (A), wherein $R^a$ in particular represents linear $C_{12}$-$C_{22}$-alkyl, or a mixture thereof, Rb in particular represents H or $C_1$-$C_4$-alkyl (more preferably H), m, n, p preferably represent, independently of one another, an integer from 2 to 5 (more preferably from 2 to 3), x, y, z preferably represent, independently of one another, a number from 0 to 50, and x+y+z preferably corresponds to a value from 5 to 50, more preferably from 8 to 25), 25 to 60 wt % of organic solvent, and further formulation auxiliaries up to 100%, wherein all components sum up to 100 wt %.

A particular embodiment of the present invention further relates to a method for preparing the inventive composition comprising the alkoxylated aliphatic alcohol. This method comprises contacting the pesticide and the alkoxylated aliphatic alcohol. Usually, the contacting takes place when preparing an agrochemical formulation by known means. The contacting of the components may be achieved by conventional equipment at any temperature, such as room temperature. Preferred mixing methods are those which are applied to prepare agrochemical compositions.

The present invention further relates to a method for preparing an aqueous tank-mix comprises the steps of
a) providing a composition containing the pesticide;
b) providing a composition containing the alkoxylated aliphatic alcohol; and
c) contacting water and the compositions of steps a) and b).

The present invention also relates to an aqueous pesticide formulation comprising a pesticide compound of the formula I as defined above in the form of fine particles suspended in an aqueous liquid.

In the aqueous pesticide formulation of the present invention, the pesticide compound of the formula I is present in the form of fine particles, which are suspended in the aqueous liquid. The average particle diameter of the fine particles will generally not exceed 10 μm and is preferably in the range from 1 to 5 μm, especially in the range from 1 to 3 μm. The average particle diameter as referred herein, is the volume average particle diameters d(0.5) or d(v, 0.5), i.e. 50 vol.-% of the particles have a diameter which is above and 50 vol.-% of the particles have a diameter which is below the value cited. Therefore, average particle diameters are also termed "volume median diameters". Such average particle diameters can be determined by dynamic light scattering (usually performed on diluted suspensions containing from 0.01 to 1% by weight of the active ingredient A). A skilled person is familiar with these methods which are described e.g. in H. Wiese (D. Distler, Ed.), Aqueous Polymer Dispersions (Wässrige Polymerdispersionen), Wiley-VCH 1999, Chapter 4.2.1, p. 40ff, and the literature cited therein; H. Auweter, D. Horn, J. Colloid Interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429. Preferably the suspended particles have a $d_{90}$-value which does not exceed 20 μm, in particular 10 μm, i.e. not more than 10 vol.-% of the particles have a diameter which is above and at least 90 vol.-% of the particles have a diameter which is below the $d_{90}$-value cited. Preferably the suspended particles have a dio-value which is not lower than 0.2 μm, in particular 0.3 μm, i.e. not more than 10 vol.-% of the particles have a diameter which is below and at least 10 vol.-% of the particles have a diameter which is above the $d_{10}$-value cited.

The amount of the pesticide compound of the formula I in the aqueous formulation is 5 to 30 wt %, in particular 6 to 20 wt %, especially 8 to 15 wt %, based on the total weight of the formulation.

The aqueous liquid may be water or a mixtures of water with water-miscible organic solvents, e.g. $C_1$-$C_4$-alkanols such as methanol, ethanol, n-propanol, isopropanol, n-butanol, 2-butanol, tert.-butanol or $C_2$-$C_4$-polyols such as ethylene glycol, propylene glyol or glycerol. In the liquid, the amount of solvent will generally not exceed 20 wt. %, based on the amount of aqueous liquid or 10 wt %, based on the weight of the formulation. Preferably, the total amount of organic solvent in the aqueous formulation will not exceed 10 wt %, in particular 5 wt %, especially 1 wt %, based on the total weight of the formulation. The amount of water is 40 to 88.9%, in particular 55 to 85.5 wt %, especially 65 to 82 wt %, based on the total weight of the formulation.

It was surprisingly found that in this particular aqueous pesticide formulation, the compound of the formula I is present in the form of an at least partially crystalline material. The at least partially crystalline material is characterized by the fact that it shows at least three, in particular at least 4 or at least 5 or at least 6 or all of the following reflexes, given in the following table 2 as 2θ values ad d spacings, when analyzing the material XRPD (X-ray powder diffractometry) at 25° C.

TABLE 2

| 2θ values and d-spacings of form A | |
|---|---|
| 2θ values | d [Å] |
| 9.7 ± 0.2° | 9.09 |
| 10.3 ± 0.2° | 8.60 |
| 11.3 ± 0.2° | 7.80 |
| 14.0 ± 0.2° | 6.34 |
| 15.5 ± 0.2° | 5.72 |
| 16.4 ± 0.2° | 5.40 |
| 17.6 ± 0.2° | 5.03 |

This at least partially crystalline form of the compound of formula I is hereinafter also termed hydrate A or form Y. Without being bound by theory, it is believed that the formation of hydrate A is due to specific interaction between the compound of formula I and the surfactant system present in the aqueous formulation. It is further believed that the specific surfactant system prevents the formation and the crystallization of the compound of formula I and thus allows the preparation of a stable aqueous formulation of the compound of formula I.

The aqueous pesticide formulation also contains from 6 to 20 wt %, in particular 8 to 17 wt %, especially 9 to 15 wt %, based on the total weight of the formulation, of at least one anionic polymeric surfactant having a plurality of $SO^{3-}$ groups. Suitable anionic polymeric surfactants. Suitable anionic polymeric surfactants having a plurality of include but are not limited to
i. condensates of arylsulfonic acid, such as benzene sulfonic acid, phenol sulfonic acid, alkylbenzene sulfonic acid (e.g. toluene sulfonic acid), naphthalene or alkylnaphthalene sulfonic acid such as $C_1$-$C_{10}$-alkylnaphthalene sulfonic acid with formaldehyde and optionally with urea and the salts thereof, e.g. the earth alkaline salts, alkaline salts or ammonium salts;
ii. lignosulfonates; and
iii. homo- and co-polymers of ethylenically unsaturated sulfonic acids, such as 2-acrylamido-2-methylpropane sulfonic acid, 2-acryloxyethane sulfonic acid, 2-acryloxy- 2-methylpropane sulfonic acid, styrenesulfonic acid or vinylsulfonic acid, opitionally in the form of a copolymer with a monoethylenically unsaturated monomer, which is e.g. selected from $C_3$-$C_5$ monoethylenically unsaturated carboxylic acid monomers such as acrylic acid or methacrylic acid, $C_1$-$C_6$-alkylesters of $C_3$-$C_5$ monoethylenically unsaturated carboxylic acid monomers such as $C_1$-$C_6$ alkylacrylates and -methacrylates, $C_2$-$C_6$-hydroxyalkylesters of $C_3$-$C_5$ monoethylenically unsaturated carboxylic acid monomers such as $C_2$-$C_6$ hydroxyalkylacrylates and -methacrylates, vinylaromatic monomers such as styrene and $C_2$-$C_{12}$-monolefines such as ethene, propene, 1-butene, isobutene, hexene, 2-ethylhexene, diisobutene (mixture of isobuten dimers), tripropene, tetrapropene, triisobutene etc.

Preferably, the anionic polymeric surfactant having a plurality of $SO^{3-}$ groups is selected from the salts of naphthalene sulfonic acid formaldehyde condensates, salts of alkylnaphthalene sulfonic acid formaldehyde condensates and the salts of naphthalene sulfonic acid formaldehyde urea co-condensates. In a particular preferred embodiment, the anionic polymeric surfactant having a plurality of $SO^{3-}$ groups is an alkaline metal salts or earth alkaline metal salts of a reaction product (condensate) of naphthalene sulfonic acid and formaldehyde; particularly suitable examples are the Morwet® grades such as Morwet® D400, D425, D440, D450 or D500(Akzo Nobel), the Tamol® NN grades of BASF SE, Surfaron® A 1530 N100 or Surfaron® A 1543 N100 (Synthron) and the Tersperse® grades such as Tersperse® 2001, 2020, 2100 or 2425 of Huntsman.

The aqueous pesticide formulation also contains from 0.1 to 10 wt %, in particular 0.5 to 8 wt %, especially 1 to 5 wt %, based on the total weight of the formulation, of a non-ionic surfactant. Suitable non-ionic surfactants include the aforementioned non-ionic surfactants. Particular preference is given to polymeric non-ionic surfactants having at least one poly($C_2$-$C_4$)alkylenoxide moiety, which are hereinafter also termed as poly($C_2$-$C_4$)alkylenoxide polymers. Examples of poly($C_2$-$C_4$)alkylenoxide polymers are non-ionic copolymers comprising ethylenoxide repeating units and $C_3$-$C_{10}$-alkylene oxide repeating units, in particular block-copolymers having at least one poly(ethylenoxide) moiety PEO and at least one polyether moiety PAO derived from $C_3$-$C_4$-alkylene oxides, in particular polyoxyethylene-polyoxypropylene-blockcopolymers. Further examples of poly($C_2$-$C_4$)alkylenoxide polymers non-ionic graft copolymers containing polyethylene oxide moiety PEO grafted on a non-ionic, hydrophilic polymeric backbone.

Amongst the poly($C_2$-$C_4$)alkylenoxide polymers particular preference is given to poly(ethyleneoxide-co-propyleneoxide) polymers, in particular to those poly(ethyleneoxide-co-propyleneoxide) polymers, wherein the ethyleneoxide and propyleneoxide repeating units are arranged blockwise.

Amongst the poly($C_2$-$C_4$)alkylenoxide polymers particular preference is given to poly(ethyleneoxide-co-propyleneoxide) polymers having a HLB value (HLB=hydrophilic-lipophilic balance) of at least 14, in particular at least 15, e.g. from 15 to 19, in particular from 15 to 19, in particular to those poly(ethyleneoxide-co-propyleneoxide) polymers, wherein the ethyleneoxide and propyleneoxide repeating units are arranged blockwise. The HLB value referred to herein is the HLB value according to Griffin (W. C. Griffin, J. Soc. Cosmet. Chem. 1, 311 (1950); 5, 249 (1954)—see also H. Mollet et al. "Formulation Technology", 1$^{st}$ ed. Wiley-VCH Verlags GmbH, Weinheim 2001, pages 70-73 and references cited therein).

Particular preference is given to aqueous formulations, where the non-ionic surfactant is selected from the group of non-ionic block-copolymers These non-ionic block copolymers of the comprise at least one poly(ethylene oxide) moiety PEO and at least one hydrophobic polyether moiety PAO. The PAO moiety usually comprises at least 3, preferably at least 5, in particular 10 to 100 repeating units (number average) which are derived from $C_3$-$C_4$ alkylene oxides, such as propylene oxide, 1,2-butylene oxide, cis- or trans-2,3-butylene oxide or isobutylene oxide. Preferably, the PAO moieties comprise at least 50% by weight, and more preferably at least 80% by weight of repeating units derived from propylene oxide. The PEO moieties usually comprise at least 3, preferably at least 5, and more preferably at least 10 repeating units derived from ethylene oxide (number average). The weight ratio of PEO moieties and PAO moieties (PEO:PAO) usually ranges from 1:10 to 10:1, preferably from 1:2 to 5:1, more preferably from 1:1 to 4:1 and in particular from 1.1:1 to 3:1. Those are preferred which have a number average molecular weight $M_N$ ranging from more than 1000 to 10000 Dalton, preferably from 1100 to 30000 Dalton, more preferably from 1200 to 20000 Dalton. In general, the PEO moieties and the PAO moieties make up at least 80% by weight, and preferably at least 90% by weight, e.g. 90 to 99.5% by weight, of the non-ionic block copolymer surfactants.

Suitable blockcopolymers are described e.g. in WO2006/002984, in particular those having the formulae P1 to P5 given therein. The non-ionic block copolymer surfactants herein are commercially available e.g. under the trade names Pluronic®, such as Pluronic® P 65, P84, P 103, P 105, P 123 and Pluronic® L 31, L 43, L 62, L 62 LF, L 64, L 81, L 92 and L 121, Pluraflo® such as Pluraflo® L 860, L1030 and L 1060; Pluriol® such as Pluriol® WSB-125, Tetronic®, such as Tetronic® 704, 709, 1104, 1304, 702, 1102, 1302, 701, 901, 1101, 1301 (BASF SE), Agrilan® AEC 167 and Agrilan® AEC 178 (Akcros Chemicals), Antarox® B/848 (Rhodia), Berol® 370 and Berol® 374 (Akzo Nobel Surface Chemistry), Dowfax® 50 C15, 63 N10, 63 N30, 64 N40 and 81 N10 (Dow Europe), Genapol® PF (Clariant), Monolan®, such as Monolan® PB, Monolan® PC, Monolan® PK (Akcros Chemicals), Panox® PE (Pan Asian Chemical Corporation), Symperonic®, such as Symperonic® PE/L, Symperonic® PE/F, Symperonic® PE/P, Symperonic® PE/T (ICI Surfactants), Tergitol® XD, Tergitol® XH and Tergitol® XJ (Union Carbide), Triton® CF-32 (Union Carbide), Teric PE Series (Huntsman) and Witconol®, such as Witconol® APEB, Witconol® NS 500 K and the like. Likewis particular preference is given to poly(ethoxylate-co-propoxylates) of $C_1$-$C_{10}$ alkanols, having a number average molecular weight MN of from 1000 to 5000 Dalton Particularly preferred examples include Atlox® G 5000 (Akzo Nobel), Tergitol®XD, Pluronic® P105 and Pluriol® WSB-125 and the like.

Preferred non-ionic graft copolymers contain, in polymerised form, (i) methyl esters or hydroxyl-$C_2$-$C_3$-alkyl esters of $C_3$-$C_5$ monoethylenically unsaturated carboxylic acid monomers, such as methyl acrylate, methyl methacrylate, hydroxyethyl acrylate and hydroxyethyl methacrylate and (ii) polyethylenoxide groups which are attached either via ester linkages or ether linkages to the polymer backbone. In a preferred embodiment, the backbone of these graft copolymers contains, in polymerized form, methyl methacrylate and polyethylene oxide esters of methacrylic acid, a particularly suitable example being Atlox® 4913 (Akzo Nobel), and the like.

The aqueous formulations according to the invention may also comprise customary additives, for example viscosity-modifying additives (thickeners), antifoams, bactericides and antifreeze agents. The amount of additives will generally not exceed 5% by weight, in particular 2% by weight of the total weight of the composition.

Suitable thickeners are compounds which confer a pseudoplastic flow behavior to the formulation, i.e. high viscosity at rest and low viscosity in the agitated stage. Mention may be made, in this connection, for example, of commercial thickeners based on polysaccharides, such as Xanthan Gum® (Kelzan® from Kelco; Rhodopol® 23 from Rhone Poulenc or Veegum® from R.T. Vanderbilt), or phyllosilicates which may be hydrophobized, such as Attaclay® (from Engelhardt). Xanthan Gum® is a preferred thickener.

Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof.

Bactericides can be added to stabilize the compositions according to the invention against attack by microorganisms. Suitable bactericides are, for example, based on isothiazolones such as the compounds marketed under the trademarks Proxel® from Avecia (or Arch) or Acticide® RS from Thor Chemie and Kathon® MK from Rohm & Haas.

The aqueous pesticide formulations of the present invention can be prepared by a process comprising the following steps:
(i) providing a suspension of the compound of formula I in a mixture of the aqueous liquid and the surfactant;
(ii) reducing the particle size of compound of formula I present in the suspension of step (i) to the desired particle size,
(iii) optionally adding further formulation auxiliaries and aqueous liquid.

In order to prepare the suspension of step (i), the pesticide compound of formula I, at lease a part of the aqueous liquid and the surfactants b) and c) are mixed in any conventional mixing device which is capable of providing sufficient shear to form the desired suspension. Suitable mixing devices include in particular high shear mixers, such as Ultra-Turrax apparatus, static mixers, e.g. systems having mixing nozzles, agitator bead mills, colloid mills con mills and other homogenizers.

In general, the sequence in which the individual components are combined is not critical. However, it may be advantageous to carry step (i) out by firstly mixing at least a part of the aqueous liquid and the surfactants until a homogenous mixture is obtained, and then adding the compound of formula I with shear to said homogenous mixture. Thus, step (i) yields a mixture of the components a), b), c) and d), wherein the compound of formula I is present in the form of solid particles which are dispersed in the homogeneous phase formed by the aqueous liquid and the surfactant. Typically, the mixture of the components a), b), c) and d) is obtained from step (i) in the form of a slurry having a content of the compound of the formula I in the range of from 5 to 40 wt %, in particular 6 to 30 wt %, especially 8 to 25 wt %, based on the total weight of the slurry.

In general, the solid compound of the formula I which is used in the preparation of the suspension of step (i) may be amorphous, crystalline or semicrystalline and is employed in particulate form, e.g. as a powder, as crystals, as a granulate or as a comminuted solidified melt. The particles of the solid active compound may be of regular or irregular shape, e.g. of spherical or virtually spherical form or in the form of needles. Generally, before being introduced in step (i), the solid insecticide compound particles essentially will have mean dimensions of more than 1 µm, e.g. in the range of from 1.5 to 1000 µm, particularly from 2 to 100 µm, and more particularly from 2.5 to 50 µm, as determined by dynamic light scattering.

The mixture obtained from step (i), i.e. in the form of a suspension, is subjected to suitable means for reducing the particle size of the a.i. particles present in the mixture to the desired particle size. The step (ii) may be carried out by any physical attrition method, such as grinding, crushing or milling, in particular by wet grinding or wet milling, including e.g. bead milling, hammer milling, jet milling, air classifying milling, pin milling, cryogenic grinding processes and the like. Steps (i) and (ii) are usually performed subsequently. However it is also possible to perform these steps together.

In a preferred embodiment of the invention, step (ii) is carried out by bead milling. In particular, bead sizes in the range of from 0.05 to 5 mm, more particularly from 0.2 to 2.5 mm, and most particularly from 0.5 to 1.5 mm have been found to be suitable. In general, bead loadings in the range of from 40 to 99%, particularly from 70 to 97%, and more particularly from 65 to 95% may be used.

Step (ii) is carried out in apparatus suitable for this purpose, in particular apparatus suitable for wet grinding or wet milling methods as necessitated by the presence of the solvent b. Such apparatus are generally known. Thus, step (ii) is preferably carried out in mills, such as ball mills or bead mills, agitator ball mills, circulating mills (agitator ball mills with pin grinding system), disk mills, annular chamber mills, double cone mills, triple roll mills, batch mills, colloid mills, and media mills, such as sand mills. To dissipate the heat energy introduced during the grinding process, the grinding chambers are preferably fitted with cooling systems. Particularly suitable is the ball mill Drais Super-flow DCP SF 12 from DRAISWERKE, INC.40 Whitney Road. Mahwah, N.J. 07430 USA, a Drais Perl Mill PMC from DRAISWERKE, INC., the circulating mill system ZETA from Netzsch-Feinmahltechnik GmbH, the disk mill from Netzsch Feinmahltechnik GmbH, Selb, Germany, the bead mill Eiger Mini 50 from Eiger Machinery, Inc., 888 East Belvidere Rd., Grayslake, Ill. 60030 USA and the bead mill DYNO-Mill KDL from WA Bachofen AG, Switzerland.

The time required for reducing the particle size depends in a manner known per se on the desired grade of fineness or the desired particle size of the active compound particle and can be determined by the person skilled in the art in standard experiments. Grinding times in the range of e.g. from 1 to 48 hours have been found to be suitable, although a longer period of time is also conceivable. A grinding time of 2 to 24 hours is preferred.

The pressure and temperature conditions during comminution are generally not critical; thus, for example, atmospheric pressure has been found to be suitable. Temperatures e.g. in the range of from 10° C. to 100° C. have been found to be suitable; the chosen temperatures are usually temperatures at which the active compound a) is present as a solid.

To the aqueous formulation obtained from step ii, further formulation additives, e.g. thickeners may be added, optionally together with further water/aqueous liquid, if repired.

The aqueous formulation shows increased storage stability, in particular no or no significant increase in particle size of the suspended particles due to unwanted Ostwald's ripening.

As pointed out above, the present invention also relates to the hydrate A as defined above. The hydrate A is an at least partly crystalline, non-stochiometric hydrate of the compound of formula I. It is believed to be stable in the aqueous pesticide formulation as described above but it appears to be instable, in the absence of the aqueous liquid and surfactant.

As pointed out above, a further aspect of the present invention relates to the hydrate B of the compound of formula I. Form B is a non-stoichiometric hydrate of the compound of formula I. The typical water content is in the range from 7.5 to 9 wt % and in particular about 8.5 wt %, i.e. 8.5±0.2 wt %. The water content can be determined by thermo-gravimetric analysis (TGA). Form B shows desolvation at a temperature in the range from 65 to 70° C., in particular 66 to 68° C. resulting in the amorphous compound of formula I. Form B is stable at room temperature in the presence of mother liquor or water but slowly converts into form C described hereinafter, when the mother liquor is removed or into amorphous material, if form B is dried.

Form B can be prepared by conventional crystallization techniques, e.g. by crystallization from a water containing organic solvent, in particular a water containing organic solvent, which is at least partially miscible with water (miscibility at least 20 wt % at 25° C.) or preferably completely miscible with water (at 25° C.). Suitable organic solvents are $C_1$-$C_4$ alkanols, such as ethanol or isopropanol, acetone, dimethyl sulfoxide, acetonitrile or cyclic ethers such as tetrahydrofurane. For obtaining form B, the water content in the water containing organic solvent is from 20 to 90 wt %.

Crystallization can be achieved by conventional techniques such as evaporation crystallization or precipitation crystallization. For precipitation crystallization or evaporation crystallization, the compound of formula I is dissolved in the water containing aqueous organic solvent or in dry organic solvent, followed by the addition of water. Crystallization can be effected by cooling or by addition of further water to reduce solubility of the compound of formula I in the water containing organic solvent. Alternatively, crystallization can be effected by removing solvent, e.g. by evaporation. Addition of seed crystals of form B will help to achieve quantitative conversion of the compound I into form B. Preferably, precipitation crystallization or evaporation crystallization is performed at temperatures in the range from 0 to 60° C., in particular from 5 to 50° C.

Form B can also be prepared by slurry crystallization, which comprises providing a slurry of the compound of formula I in water or in the water containing organic solvent. Thereby, the solid compound of formula I converts into form B. For the purpose of slurry cristallization, aqueous organic solvents or water can be used. The amount of water in the solvent used for slurry cristallization may range from 10 to 100 wt %. Suitable organic solvents are $C_1$-$C_4$ alkanols, such as ethanol or isopropanol, ethylene glycol, glycerol, acetone, dimethyl sulfoxide, acetonitrile or cyclic ethers such as tetrahydrofurane. Preferably,slurry crystallization is performed at temperatures in the range from 0 to 60° C., in particular from 5 to 50° C. The time required for conversion into form B may be range from 1 h to 10 d, depending on the temperature and the solvent. Conversion into form B can be accelerated by excerting mechanical shear to the slurry, e.g. by milling. Addition of seed crystals of form B will help to achieve quantitative conversion of the compound I into form B.

As a starting material for crystallization, any crystalline or amorphous form of the compound of the formula I can be used.

Form B is stable at room temperature when in contact with aqueous solvent or water or at high degrees of humidity, e.g. 90%, but slowly converts into form C described hereinafter, when the mother liquor is removed or humidity is reduced. Form B slowly converts into amorphous material, if form B is dried at elevated temperatures, e.g. >50° C. Form B may provide superior formulation stability to aqueous formulations.

Yet, a further aspect of the present invention relates to a hydrate C of the compound of formula I. Form C is a further non-stoichiometric hydrate of the compound of formula I. The typical water content is in the range from 6.5 to 8 wt % and in particular about 7.6 wt %, i.e. 7.6±0.2 wt %. The water content can be determined by thermogravimetric analysis (TGA). Form C shows desolvation at a temperature in the range from 55 to 60° C., in particular 56 to 58° C. resulting in the amorphous compound of formula I.

Form C can be obtained from form B by removing the mother liquor from the crystalline material of form B and storing the thus obtained solids at ambient conditions (e.g. 5 to 30° C., humidity 10 to <90%). Form C can also be obtained as an intermediate in the slurry experiments for the production of form B.

Form C is stable at ambient conditions over weeks and month and thus it is particularly useful for preparing solid formulations of the compound of formula I.

The following figures and examples further illustrate the present invention:

FIG. 1: X-ray Powder Diffractogramm (XRPD) of Form A, obtained from the suspension concentrate of example 1.

Figure 2:
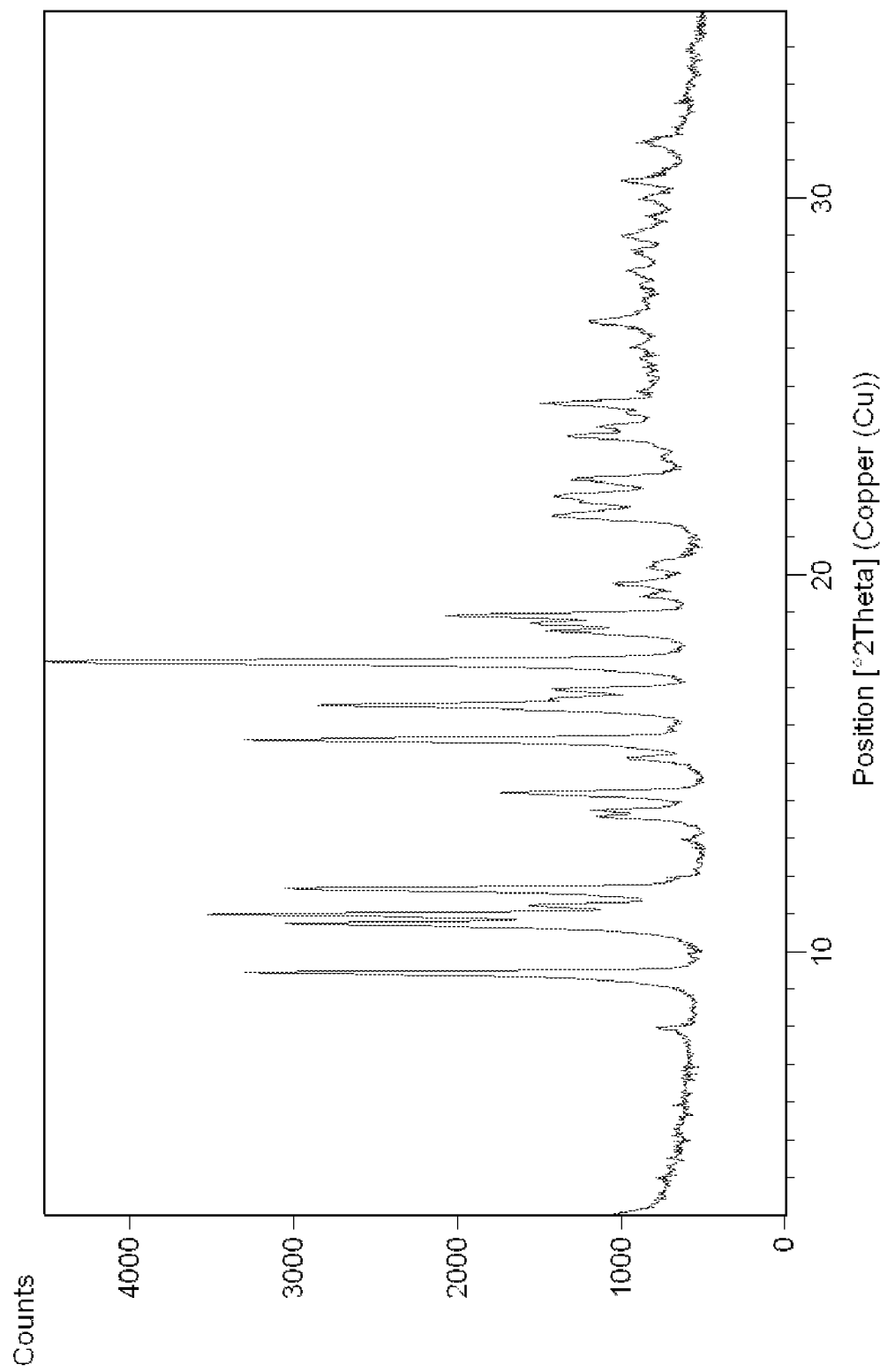

FIG. 2: X-ray powder diffractogramm (XRPD) of Form B.

Figure 3:
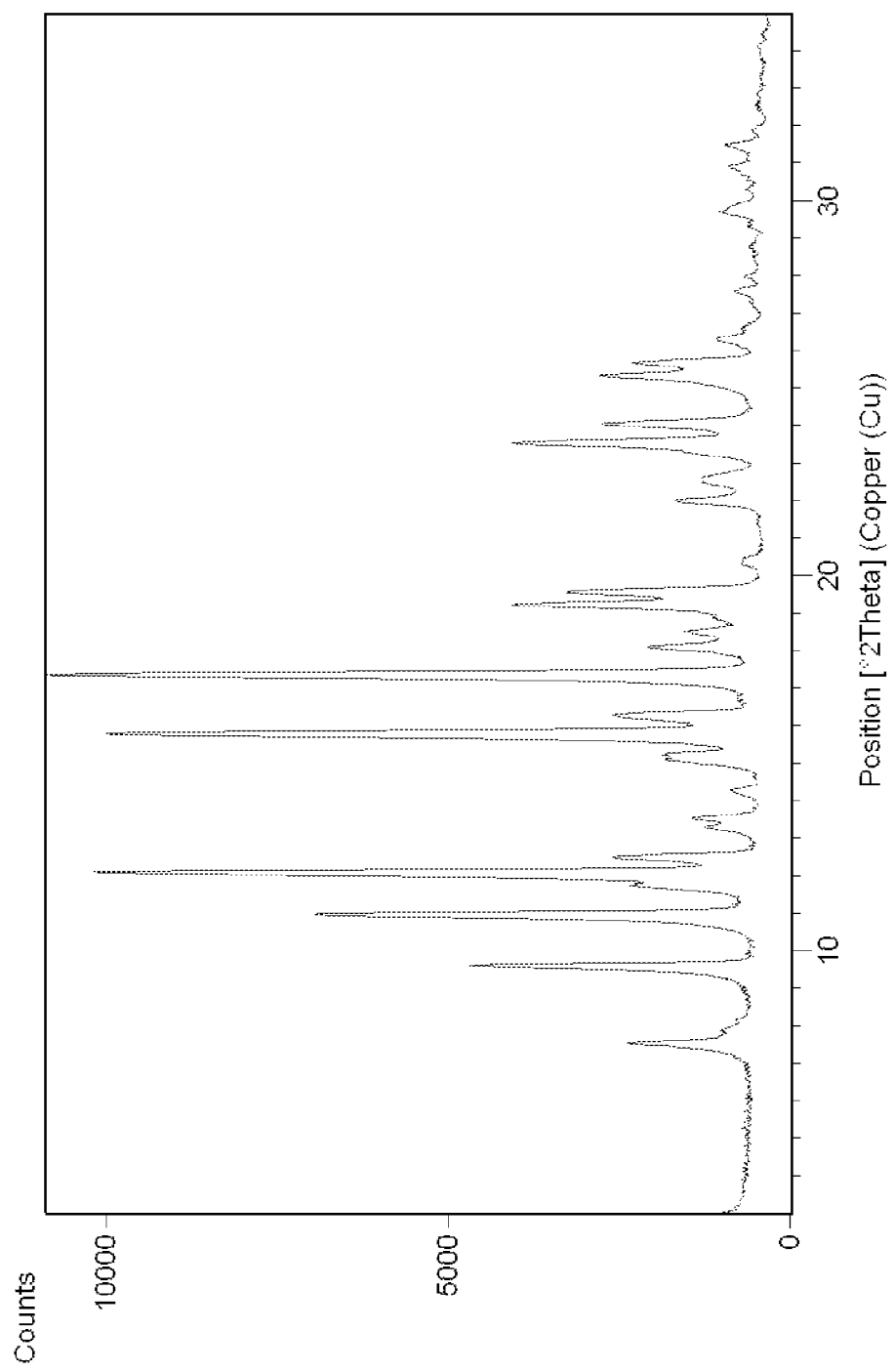

FIG. 3: X-ray powder diffractogramm (XRPD) of Form C.

EXAMPLES

Starting Materials:
Insecticide A: Insecticide of formula (I).
Insecticide B: Insecticide of formula (II).
Adjuvant A: 83% parafin base petroleum oil, 17% sorbitan fatty acid ester and polyethoxylated sorbitan fatty acid ester, commercially available as Agridex® from Bayer Crop Science.
Adjuvant B: Polyalkyleneoxide modified polydimethylsiloxane, poly(ethylene oxide-block-propylene oxide, and as minor antifoaming polypropylene oxide oleate butyl ether, commercially available as Kinetic® Molecular Zippering Action from Helena.
Adjuvant C: linear $C_{16}/C_{18}$ alcohol, ethoxylated and propoxylated, liquid at room temperature, wetting power by immersion: >240 s (according to DIN 1772 at room temperature at 1 g/L in 2 g/l sodium carbonate), water content 5-10 wt %, surface tension: 30-35 mN/m (according to DIN 14370 at room temperature at 1 g/L), pH in water about 7.
Surfactant 1: Sodium salt of a naphthalene sulfonic acid formaldehyde condensate—Morwet® D425 (Akzo Nobel).
Surfactant 2: $C_1$-$C_9$-alkylether of poly-$C_2$-$C_3$-alkylene glycol (MN 2900)—Atlox® G5000 (Croda), HLB 17.
Surfactant 3: Polyoxyethylene graft copolymer Atlox® 4913, Croda.
Antifoaming agent: Silicon based defoamer.
Preservative: Acticide MBS (Thor).
Thickener: Xanthan Gum.
Analytics:
The X-ray powder diffractograms (XRPD) reported herein and displayed in FIGS. 1, 2 and 3 were recorded using a Panalytical X"Pert Pro diffractometer (manufacturer: Panalytical) in reflection geometry in the range from 2θ=3°-35° C. with increments of 0.0167° C. using Cu—Kα radiation (at 25° C.). The recorded 2θ values were used to calculate the stated interplanar spacings d. The intensity of the peaks (y-axis: linear intensity counts) is plotted versus the 2θ angle (x-axis in degrees 2θ).

DSC was performed on a Mettler Toledo DSC 822e module. Than samples were placed in crimped but vented aluminum pans. The samples size in each case was 5 to 10 mg. The thermal behaviour was analized in the range 30-250° C. The heating rate was 5° C./min. The samples were purged with a stream of nitrogen flowing at 150 ml/during the experiment.

Melting points values were confirmed by a Mettler Hot Stage in combination with a light microscope.

Particle Size Distributions were determined by using a Malvern Mastersizer 2000.

Example 1

Stable Suspension Concentrate

A suspension concentrate (SC A) having the following composition was prepared by wet bead milling: 9.4 wt % Insecticide A, 3 wt % surfactant 2, 10 wt % surfactant 1, 0.2 wt % xanthan gum, 0.4 wt % antifoaming agent, 0.16 wt % preservative and water up to 100 wt %. The mean particle size was about 1 to 2 µm.

The formulation was prepared as follows: Insecticide A, surfactant 1, surfactant 2, part of water, part of defoamer and preservative were mixed together in a suitable container using a Silverson high shear mixer. The mixture was then ground in a bead mill with sufficient ball loading to ensure effective milling efficiency. The temperature of grinding head was controlled at 5° C. The milling was stopped when the desired particle size distribution had been obtained (measured with Malvern Mastersizer 2000). Finally, the thickener, the remaining anti foaming agent and was added to the above sample with stirring to ensure homogeneous distribution of components.

Samples of the thus obtained aqueous formulation were stored for 3 month at different storage conditions and before and thereafter analyzed with regard to the particle size of the suspended particles. The results are summarized in table 3:

TABLE 3

Storage conditions and particle size distribution

| Storage Temperature (° C.) | Particle Size (µm) | | |
|---|---|---|---|
| | $d_{10}$ | $d_{50}$ | $d_{90}$ |
| initial | 0.741 | 2.076 | 6.037 |
| −10 | 0.716 | 1.993 | 5.735 |
| 5 | 0.702 | 1.977 | 5.774 |
| Freeze/Thaw [1)] | 0.649 | 1.769 | 5.045 |
| 25 | 0.663 | 1.811 | 5.155 |
| 40 | 0.705 | 1.824 | 4.814 |
| 54 | 0.857 | 2.370 | 6.072 |

[1)] cycling from −5° C. to 30° C. each 24 h.

Two further samples were stored at −20° C. as well as 60° C. for one month, respectively. The crystal form before/after storage was characterized by XRPD. The X-ray powder diffractogram, measured at 25° C. and Cu—K$_\alpha$ radiation, before storage is depicted as FIG. 1 and shows the following reflexes, given as 2θ values: 9.7±0.2°, 10.3±0.2°, 11.3±0.2°, 14.0±0.2°, 15.5±0.2°, 16.4±0.2°, 17.6±0.2°. A similar XRPD was found after storage with same reflexes, indicating that the form A was present in the formulation before and after storage.

Comparative Example C1

A suspension concentrate (SC B) having the following composition was prepared by wet bead milling: 9.4 wt % Insecticide A, 3 wt % surfactant 2, 10 wt % surfactant 3, 0.2 wt % xanthan gum, 0.4 wt % antifoaming agent, 0.15 wt % preservative, 10 wt % urea and water up to 100 wt %. The mean particle size ($d_{50}$) was about 1 to 2 µm.

Upon storage at 54° C. for two weeks, a significant increase in particle size was observed. The increase of the $d_{50}$ value was more than 50% of the initial value.

Example 2

Efficacy Improvement of SC Formulation with Tank Mix Adjuvant

A suspension concentrate (SC A) having the following composition was prepared by wet bead milling: 9.4 wt % Insecticide A, 3 wt % poly(ethylene glycol-block-propylene glycol), 10 wt % naphthalene sulfonate condensate salt, 0.2% xanthan gum, 0.4 wt % antifoaming agent, 0.16 wt % preservative and water up to 100 wt %. The mean particle size was about 1 to 2 µm. SC A was mixed before application with water to give a spray mix with the desired concentration of Insecticide A. Then Adjuvant A or B was added to the above composition at desired concentration. Following conditions were used: spray volume 300 l/ha, Insecticide A use rate 10 g/ha, concentration of Adjuvant A or B in spray mix 1 wt % or 0.25 wt %, respectively, 0.25%, or 0.1%, respectively.

Spray application and biological testing: The spray application was conducted in a spray chamber with said spray mix. Pepper plants, variety California Wonder, were sprayed using a 'U'-shaped boom equipped with three nozzles that sprayed the upper and lower leaf surfaces. Each treatment was replicated four fold, one replicate represents one pepper plant. Treated pepper plants were held in a greenhouse that allowed UV penetration. Plants were then infested with green peach aphids at various intervals after treatment (2, 7 and 15 days; DAT). The treated plant that were subsequently infested were held in a holding room at 27° C. under constant fluorescent light for 6 days and then percent control was assessed by comparing the number of live aphids relative to the control plants. The results are summarized in Table 4. It was found significant efficacy improvement for the composition containing the adjuvant in comparison with the composition without adjuvant.

TABLE 4

Aphids control [%] with suspension concentrate

| Adjuvant | 2 DAT | 7 DAT | 15 DAT |
|---|---|---|---|
| — [a)] | 49 | 70 | 9 |
| 1 wt % Adjuvant A | 99 | 100 | 99 |
| 0.25 wt % Adjuvant B | 68 | 100 | 82 |

[a)] without adjuvant.

Example 3

Efficacy Improvement of EC Formulation with Built-In Adjuvant

An emulsion concentrate (EC A) having the following composition was prepared from 5.0 wt % Insecticide A, 6 wt % calcium salt of dodecylbenzene sulfonic acid, 11.5 wt % iso-$C_{13}$ alcohol ethoxylated (surface tension 27-29 mN/m according to DIN 53914, at 1 g/l at 23° C. in distilled water), 8 wt % poly(ethylene glycol-block-propylene glycol), 30 wt % Adjuvant B, 10,5 wt % 2-heptanone, and 29 wt % heavy aromatic solvent naphtha (initial boiling point 240° C.). A comparative EC Comp1 was prepared as EC A, wherein Adjuvant B was substituted by the corresponding amount of heavy aromatic solvent naphtha.

EC A was mixed before application with water to give a spray mix with the desired concentration of Insecticide A. Following conditions were used: spray volume 300 l/ha, Insecticide A use rate 10 g/ha. The spray application and biological testing were performed as described in Example 2. The results are summarized in Table 5. It was found that the adjuvant B significantly improves efficacy of the formulations in comparison with formulations without adjuvant B.

TABLE 5

| Aphids control [%] with emulsion concentrate | | | |
|---|---|---|---|
| Formulation | 2 DAT | 7 DAT | 15 DAT |
| EC Comp1 [a] | 95 | 95 | 22 |
| EC A | 100 | 100 | 100 |

[a] comparative, not according to the invention.

Example 4

Efficacy Improvement of ME Formulation with Tank Mix Adjuvant

A miniemulsion/microemulsion (ME A) having the following composition was prepared from 5.0 wt % Insecticide A, 6 wt % calcium salt of dodecylbenzene sulfonic acid, 13 wt % ethoxylated iso-$C_{13}$ alcohol (surface tension 27-29 mN/m according to DIN 53914, at 1 g/l at 23° C. in distilled water), 4 wt % triblockpolymer EO/PO/EO, 12 wt % 2-heptanone, 18 wt % heavy aromatic solvent naphtha (initial boiling point 240° C.), 20 wt % propylene glycol, 0.02 wt % citric acid monohydrate, 0.2 wt % biocide, and water up to 100 wt %.

ME A was mixed before application with water to give a spray mix with the desired concentration of Insecticide A. Following conditions were used: spray volume 300 l/ha, Insecticide A use rate 10 g/ha, Adjuvant A 1 wt %. The spray application and biological testing were performed as described in Example 2. The results are summarized in Table 6. It was found that the adjuvant A significantly improves efficacy if the formulation in comparison with formulations without adjuvant A.

TABLE 6

| Aphids control [%] with miniemulsion | | | |
|---|---|---|---|
| Adjuvant | 2 DAT | 7 DAT | 15 DAT |
| — [a] | 100 | 93 | 73 |
| 1 wt % Adjuvant A | 100 | 100 | 98 |

[a] comparative, not according to the invention.

Example 5

Efficacy Improvement of SC formulation with Tank Mix Adjuvant

The suspension concentrate SC A of example 2 was mixed before application with water to give a spray mix with the desired concentration of Insecticide A. Then adjuvant C was added to the above mixture at desired concentration. Following conditions were used: spray volume 300 l/ha, Insecticide A use rate 10 g/ha, concentration of adjuvant C in spray mix 1%, 0.25%, or 0.1%, respectively.

Spray application and biological testing: The spray application was conducted in a spray chamber with said spray mix. Pepper plants, variety California Wonder, were sprayed using a 'U'-shaped boom equipped with three nozzles that sprayed the upper and lower leaf surfaces. Each treatment was replicated four fold, one replicate represents one pepper plant. Treated pepper plants were held in a greenhouse that allowed UV penetration. Plants were then infested with green peach aphids at various intervals after treatment (2, 7 and 15 days; DAT). The treated plant that were subsequently infested were held in a holding room at 27° C. under constant fluorescent light for 6 days and then percent control was assessed by comparing the number of live aphids relative to the control plants.

The results are summarized in Table 7. It was found that the adjuvant C at all concentrations significantly improves efficacy of the formulation in comparison with formulations without adjuvant C.

TABLE 7

| Aphids control [%] with SC A | | | |
|---|---|---|---|
| Adjuvant C | 2 DAT | 7 DAT | 15 DAT |
| — [a] | 49 | 70 | 9 |
| 1 wt % | 90 | 100 | 100 |
| 0.25 wt % | 83 | 100 | 99 |
| 0.1 wt % | 78 | 100 | 97 |

[a] without adjuvant.

Example 6

Efficacy Improvement of EC Formulation with Built-In Adjuvant

An emulsion concentrate (EC B) having the following composition was prepared from 5.0 wt % Insecticide A, 6 wt % polyarylphenyl ether sulfate ammonium salt, 11.5 wt % aliphatic alcohol ethoxylated with an average of 5 mol EO (HLB value 10-11), 8 wt % poly(ethylene glycol-block-propylene glycol)1, 20 wt % adjuvant C, 10,5 wt % 2-heptanone, and 39 wt % heavy aromatic solvent naphtha (initial boiling point 240° C.). A comparative formulation "EC Comp2" was prepared as EC B, wherein the adjuvant C was substituted by the corresponding amount of heavy aromatic solvent naphtha.

EC A was mixed before application with water to give a spray mix with the desired concentration of Insecticide A. Following conditions were used: spray volume 300 l/ha, 1500 l/ha respectively. Insecticide A use rate 10 g/ha. The spray application and biological testing were performed as described in Example 5. The results are summarized in Table 8. It was found that the adjuvant C significantly improves efficacy of the formulation in comparison with formulations without adjuvant C.

TABLE 8

Aphids control [%] with emulsion concentrate

| Formulation | 2 DAT | 7 DAT | 15 DAT |
|---|---|---|---|
| EC Comp2 (300 l/ha) [a] | 95 | 95 | 22 |
| EC B (300 l/ha) | 99 | 100 | 91 |
| EC Comp2 (1500 l/ha) [a] | 92 | 76 | 50 |
| EC B (1500 l/ha) | 96 | 99 | 85 |

[a] without adjuvant

Example 7

Efficacy Improvement of SC Formulation with Tank Mix Adjuvant

Adjuvant mixture D was prepared by mixing 50 wt % adjuvant C, 10 wt % Atplus® 300E-SP (from Croda, a low moisture blend of calcium dodecyl benzene sulfonate and sorbitan trioleate, and polyoxyethylsorbitan fatty acid esters), and 40 wt % low molecular weight paraffinic oil (CAS 64741-89-5).

Adjuvant mixture E was prepared by mixing 50 wt % adjuvant C, 10 wt % Atplus® 300F-SP and 40 wt % low molecular weight paraffinic oil (boiling point 270-320° C.).

SC A (from example 2) was mixed before application with water to give a spray mix with the desired concentration of active ingredient. Then either adjuvant mixture D or adjuvant mixture E was added to the above mixture at desired concentration. In this experiment, following conditions were used: spray volume 300 l/ha, active ingredient use rate 10 g/ha, concentration of Adjuvant mixture A or B 0.2 wt %.

The spray application and biological testing were performed as described in Example 5. The results are summarized in Table 9. A significant improvement of efficacy was found for the compositions containing the adjuvants in comparison with the composition without adjuvant.

TABLE 9

Aphids control [%] with SC A

| Formulation | 2 DAT | 7 DAT | 15 DAT |
|---|---|---|---|
| SC A [a] | 49 | 70 | 9 |
| SC A + Adjuvant mixture D | 99 | 100 | 100 |
| SC A + Adjuvant mixture E | 100 | 99 | 100 |

[a] without adjuvant

Example 8

Efficacy Improvement of SC Formulation with Tank Mix Adjuvant

Adjuvant mixture F was prepared by mixing 50 wt % adjuvant C and 50 wt % linear fatty alcohol alkoxylate (wetting 22-32 s, according to EN 1772 at room temperature at 1 g/L). Adjuvant mixture G was prepared by mixing 90 wt % adjuvant C and 10 wt % fatty alcohol alkoxylate (same as in mixture F). Adjuvant mixture H was prepared by mixing 75 wt % Alcohol alkoxlyate A and 25 wt % fatty alcohol alkoxylate (same as in mixture F).

SC A (from example 2) was mixed before application with water to give a spray mix with the desired concentration of active ingredient. Then Adjuvant mixture F, G, or H was added to the above mixture at desired concentration. In this experiment, following conditions were used: spray volume 300 l/ha, active ingredient use rate 10 g/ha, concentration of Adjuvant mixture F, G, or H 0.1 wt %.

The spray application and biological testing were performed as described in Example 5. The results are summarized in Table 10. A significant improvement of efficacy was found for the compositions containing low amounts of the adjuvants in comparison with the composition without adjuvant.

TABLE 10

Aphids control [%] with SC A

| Formulation | 2 DAT | 7 DAT | 15 DAT |
|---|---|---|---|
| SC A [a] | 49 | 70 | 9 |
| SC A + Adjuvant mixture F | 100 | 99 | 97 |
| SC A + Adjuvant mixture G | 100 | 99 | 99 |
| SC A + Adjuvant mixture H | 100 | 99 | 100 |

[a] without adjuvant

Example 9

Efficacy Improvement of EC Formulation with Built-In Adjuvant

An emulsion concentrate (EC C) having the following composition was prepared from 5.5 wt % Insecticide A, 14 wt % polyarylphenyl ether sulfat ammonium salt, 8 wt % poly(ethylene glycol-block-propylene glycol), 40 wt % branched fatty alcohol alkoxylate (wetting power by immersion 10-100 s according to DIN 1772 at room temperature at 1 g/L in 2 g/l sodium carbonate; surface tension: 20-29 mN/m (according to DIN 14370 at room temperature at 1 g/L)), 14 wt % 2-heptanone, and 19 wt % heavy aromatic solvent naphtha (initial boiling point 240° C.).

A comparative EC Comp3 was prepared as EC C, wherein the branched fatty alcohol alkoxylate was substituted by the corresponding amount of heavy aromatic solvent naphtha.

EC C was mixed before application with water to give a spray mix with the desired concentration of Insecticide A. Following conditions were used: spray volume 300 l/ha. Insecticide A use rate 10 g/ha. The spray application and biological testing were performed as described in Example 2. The results are summarized in Table 11.

TABLE 11

Aphids control [%] with emulsion concentrate

| Formulation | 2 DAT | 7 DAT | 15 DAT |
|---|---|---|---|
| EC Comp3 | 95 | 95 | 22 |
| EC B [a] | 99 | 100 | 91 |
| EC C | 96 | 95 | 35 |

[a] see Example 6

Example 9

Efficacy Improvement of EC Formulation without Built-In Adjuvant

An emulsion concentrate (EC D) having the following composition was prepared from 5 wt % Insecticide B, 14 wt % polyarylphenyl ether sulfat ammonium salt, 8 wt % poly(ethylene glycol-block-propylene glycol), 14 wt % 2-heptanone, and 59 wt % heavy aromatic solvent naphtha (initial boiling point 240° C.).

EC D was mixed before application with water (comparative) or with water containing 0.5% v/v of either adjuvant A or adjuvant C to give a spray mix with the desired concentration of Insecticide A. Following conditions were used: spray volume 300 l/ha. Insecticide A use rate 0.3 g/h or 10 g/ha. The spray application and biological testing were performed as described in Example 2. The results are summarized in Table 11.

TABLE 11

Aphids control [%] with emulsion concentrate

| Formulation | Adjuvant | Appl. Rate | 1 DAT | 7 DAT |
| --- | --- | --- | --- | --- |
| EC D[a)] | — | 0.3 g/ha | 10 | 18 |
| EC D[a)] | — | 10 g/ha | 62 | 24 |
| EC D | A | 0.3 g/ha | 68 | 15 |
| EC D | A | 10 g/ha | 69 | 27 |
| EC D | C | 0.3 g/ha | 100 | 39 |
| EC D | C | 10 g/ha | 100 | 54 |

[a)]comparative

Example 10

Preparation of form B by Slurry Experiments

Amorphous compound of formula I or the compound of formula I in the form of a mixture of amorphous and partly crystalline material was suspended in water or aqueous solvent as given in the following table 12 with stirring. After the time period given in table 12 the slurry was filtered and the resulting material was immediately subjected to analysis by subjected to analysis by X-ray powder diffractometry at 25° C. and Cu—$K_\alpha$ radiation. In each case, form B was obtained. In Example 10-L the suspension was subjected to milling as described for example 1.

TABLE 12

| Example 10 | Solvent | T [° C.] | Experiment |
| --- | --- | --- | --- |
| A | Water/Tetrahydrofuran (95:5 v/v) | 22 | Slurry, 6 d |
| B | Ethyleneglychol/Water (1:1 v/v) | 22 | Slurry, 1 d |
| C | Acetone/Water (1:1 v/v) | 22 | Slurry, 7 d |
| D | Ethyleneglychol/Water (1:1 v/v) | 22 | Slurry, 1 week |
| E | Glycerin/Water (1:1 v/v) | 22 | Slurry, 1 week |
| F | Ethyleneglychol/Water (1:1 v/v) | 22 | Slurry, 5 weeks |
| G | Glycerin/Water (1:1 v/v) | 22 | Slurry, 5 weeks |
| H | Isopropanol/Water (1:1 v/v) | 22 | Slurry, 1 d |
| J | Water | 22 | Slurry, 1 d |
| K | Water | 40 | Slurry, 1 h |
| L | Water/EtOH (9:1 v/v) | 22 | Milling of slurry, 1 h |
| M | Water/MeOH (3:7 v/v) | 22 | Slurry, 1 d |

The thus obtained hydrate form B has a X-ray powder diffractogram as shown in FIG. 2. The XRPD (at 25° C. and Cu—$K_\alpha$ radiation) showed the following reflexes, given as 2θ values: 8.0±0.2°, 9.5±0.2°, 10.7±0.2°, 11.0±0.2°, 11.2±0.2°, 11.7±0.2°, 14.2±0.2°, 15.6±0.2°, 16.5±0.2°, 17.7±0.2°, 21.5±0.2°.

Example 11

Preparation of Form B by Precipitation Experiments

The compound of formula I in the form of a mixture of amorphous and partly crystalline material was dissolved at 22° C. in the organic solvent as given in the following table 13 with stirring. Then, water was added dropwise with stirring until precipitation occurs. The precipitated material was filtered of and immediately subjected t subjected to analysis by X-ray powder diffractometry at 25° C. and Cu—$K_\alpha$ radiation. In each case, form B was obtained.

TABLE 13

| Example 11 | Solvent | T [° C.] |
| --- | --- | --- |
| A | Isopropanol | 22 |
| B | dimethylsulfoxide | 22 |

Example 12

Preparation of Form C by Drying of Form B

Form B obtained from Example 11 was left for 16 h at ambient conditions on filter paper. The thus obtained material was subjected to analysis by X-ray powder diffractometry at 25° C. and Cu—$K_\alpha$ radiation. The thus obtained XRPD showed the following reflexes, given as 2θ values: 7.5±0.2°, 9.6±0.2°, 11.0±0.2°, 11.7±0.2°, 12.1±0.2°, 12.5±0.2°, 15.8±0.2°, 16.3±0.2°, 17.4±0.2°, 19.3±0.2° and 19.6±0.2°.

Example 13

Preparation of Form C by Slurry Experiments followed by Drying

Amorphous compound of formula I or the compound of formula I in the form of a mixture of amorphous and partly crystalline material was suspended in water or aqueous solvent as given in the following table 14 with stirring for at least 2 d. Then, the slurry was filtered and the resulting material was left for 16 h at ambient conditions on filter paper. The thus obtained material was subjected to analysis by X-ray powder diffractometry at 25° C. and Cu—$K_\alpha$ radiation. In each case, form C was obtained.

TABLE 14

| Example 13 | Solvent | T [° C.] |
| --- | --- | --- |
| A | Water | 22 |
| B | Water/Tetrahydrofuran (95:5 v/v) | 22 |

We claim:

1. A composition comprising a pyripyropene pesticide of formula I or of formula II Formula I

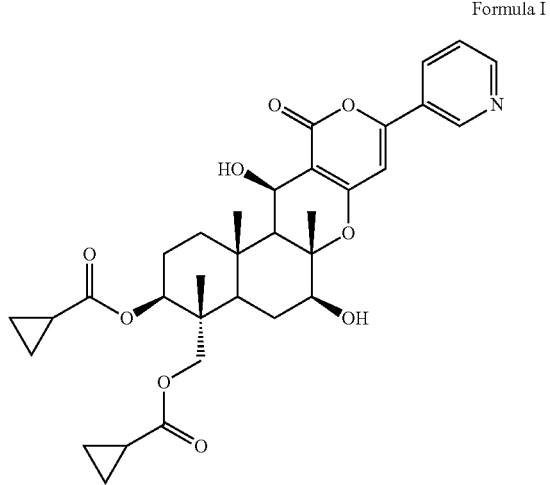

Formula II

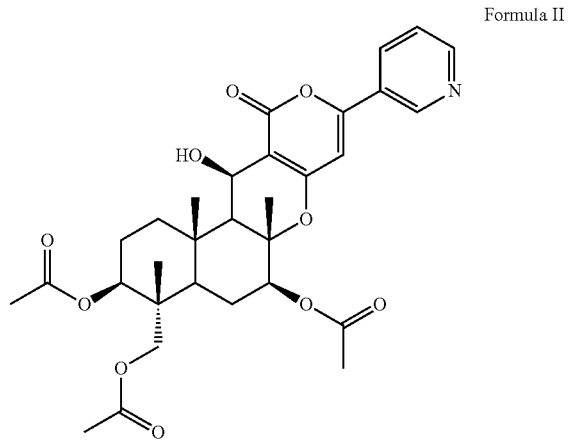

or crystalline hydrates thereof;
and an adjuvant, where the composition is in the form of an emulsifiable concentrate comprising at least 10 wt % of the adjuvant, based on the composition and where the adjuvant comprises
an alkoxylated aliphatic alcohol.

2. The composition according to claim 1, wherein the pyripyropene pesticide is the pesticide of formula I.

3. The composition according to claim 1, further comprising a surfactant which carries at least one poly-$C_2$-$C_4$-alkyleneoxide moiety selected from polyethoxylated sorbitan fatty acid esters, poly(ethyleneoxide-co-propylenoxide) copolymers and poly-$C_2$-$C_4$-alkyleneoxide modified polydimethylsiloxanes.

4. The composition according to claim 1, further comprising a silicone-based adjuvant.

5. The composition according to claim 1, further comprising a silicone-based adjuvant comprising a poly-$C_2$-$C_4$-alkyleneoxide modified polydimethylsiloxane.

6. The composition according to claim 1, further comprising a crop oil concentrate.

7. The composition according to claim 6, wherein the crop oil concentrate contains at least one hydrocarbon solvent and at least one non-ionic surfactant.

8. The composition according to claim 1, wherein the alkoxylated aliphatic alcohol is selected from alkoxylates of the formula (A)

$$R^a\text{—}O\text{—}(C_mH_{2m}O)_x\text{—}(C_nH_{2n}O)_y\text{—}(C_pH_{2p}O)_z\text{-}R^b \quad (A)$$

in which
$R^a$ represents $C_5$-$C_{36}$-alkyl, $C_5$-$C_{36}$-alkenyl or a mixture thereof;
$R^b$ represents H or $C_1$-$C_{12}$-alkyl;
m,n,p represent, independently of one another, an integer from 2 to 16;
x, y, z represent, independently of one another, a number from 0 to 100; and
x+y+z corresponds to a value from 1 to 100.

9. The composition according to claim 8, wherein $R^a$ represents a linear $C_5$-$C_{36}$-alkyl, $C_5$-$C_{36}$-alkenyl, or a mixture thereof.

10. The composition according to claim 8, wherein $R^a$ represents a linear $C_{14}$-$C_{36}$-alkyl, $C_{14}$-$C_{36}$-alkenyl, or a mixture thereof.

11. The composition according to claim 8, wherein m, n, p represent, independently of one another, an integer from 2 to 5.

12. The composition according to claim 8, wherein x+y+z corresponds to a value from 10 to 30.

13. A composition comprising a pyripyropene pesticide of formula I or of formula II Formula I

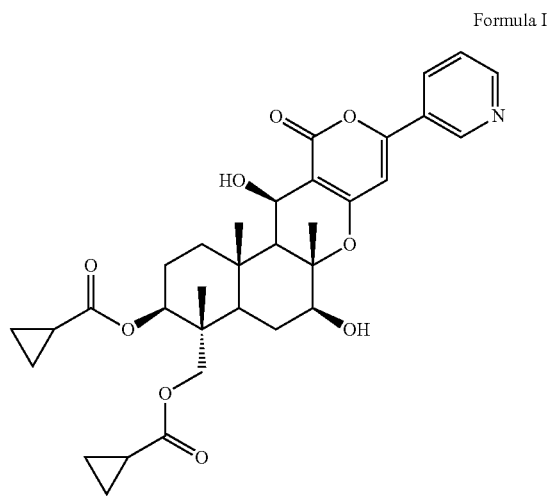

Formula II

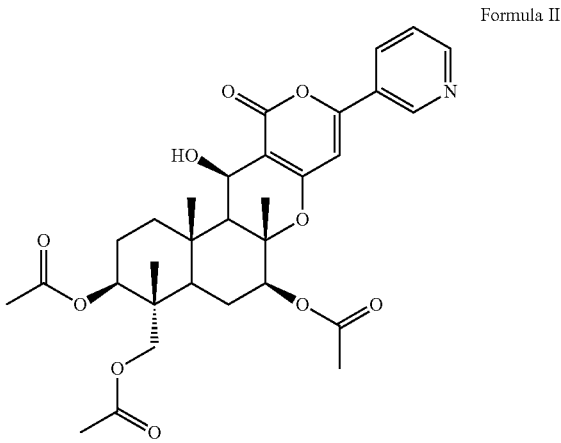

and an adjuvant, where the composition is in the form of a tank-mix, which contains 0.01 to 5 wt %, based on the total weight of the tank mix of the adjuvant and where the adjuvant comprises an alkoxylated aliphantic alcohol.

14. The composition according to claim 13, further comprising a crop oil concentrate.

15. The composition according to claim 13, further comprising a silicone-based adjuvant comprising a poly-$C_2$-$C_4$-alkyleneoxide modified polydimethylsiloxane.

16. The composition according to claim 1, wherein the pesticide is present in dissolved form or in suspended form.

17. A method for preparing the composition as defined in claim 1, which method comprises contacting said pesticide and said adjuvant.

18. A method for preparing an aqueous tank-mix comprising the steps of
   a) providing a composition containing a pesticide of formula I or of formula II

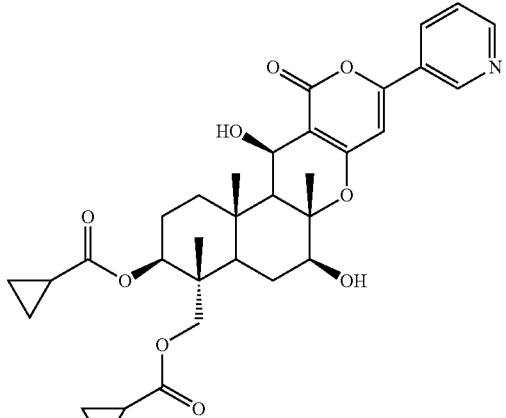

Formula I

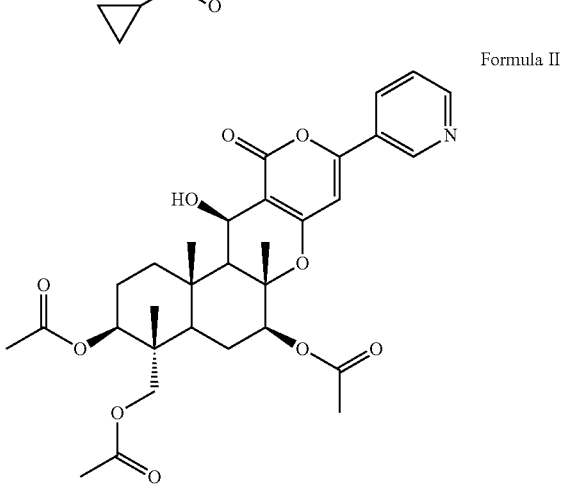

Formula II

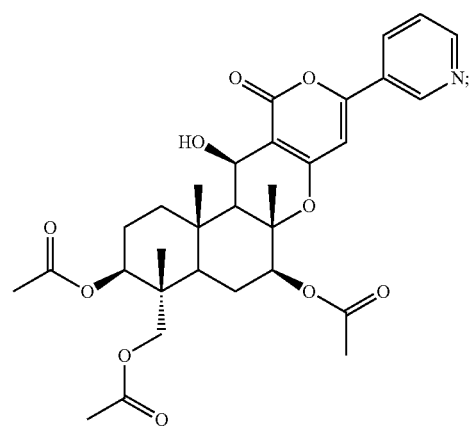

b) providing a composition containing an adjuvant, which is an alkoxylated aliphantic alcohol; and
   c) contacting compositions of steps a) and b).

19. Kit of parts comprising, as separate components,
   a) a pesticide of formula I or of formula II Formula I

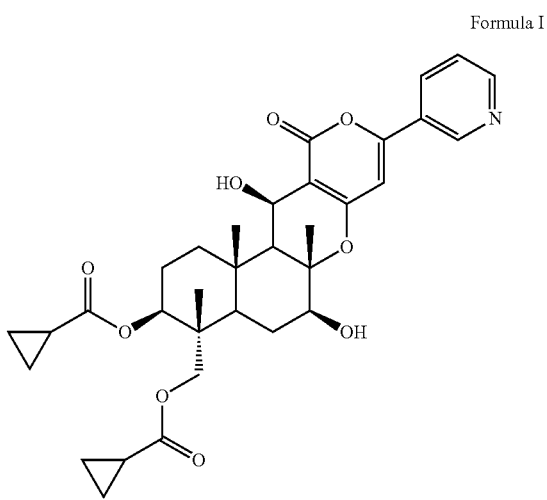

Formula II b) an adjuvant, which is an alkoxylated aliphatic alcohol for combined use.

20. The composition of claim 1, wherein the pyripyropene pesticide is a crystalline hydrate of the compound of formula I Formula I which, in an X-ray powder diffractogram at 25° C. and Cu—K$_\alpha$ radiation, shows at least four of the following reflexes, given as 2θ values: 9.7±0.2°, 10.3±0.2°, 11.3±0.2°, 14.0±0.2°, 15.5±0.2°, 16.4±0.2°, 17.6±0.2°.

21. The composition of claim 1, wherein the pyripyropene pesticide is a crystalline hydrate of the compound of formula I

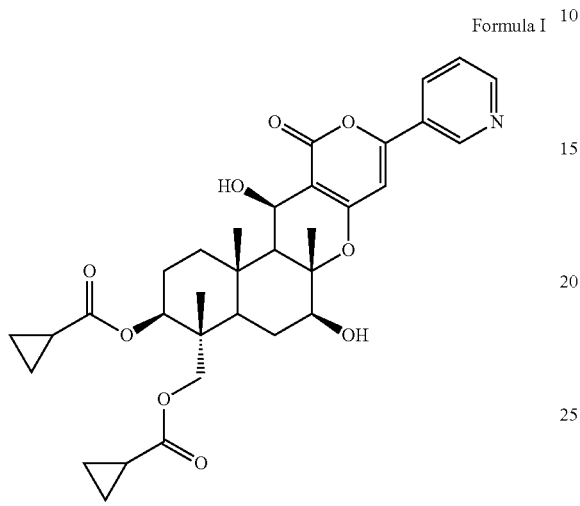

Formula I which, in an X-ray powder diffractogram at 25° C. and Cu—K$_\alpha$ radiation, shows at least four of the following reflexes, given as 2θ values: 8.0±0.2°, 9.5±0.2°, 10.7±0.2°, 11.0±0.2°, 11.2±0.2°, 11.7±0.2°, 14.2±0.2°, 15.6±0.2°, 16.5±0.2°, 17.7±0.2°, 21.5±0.2°.

22. The composition of claim 1, wherein the pyripyropene pesticide is a crystalline hydrate of the compound of formula I

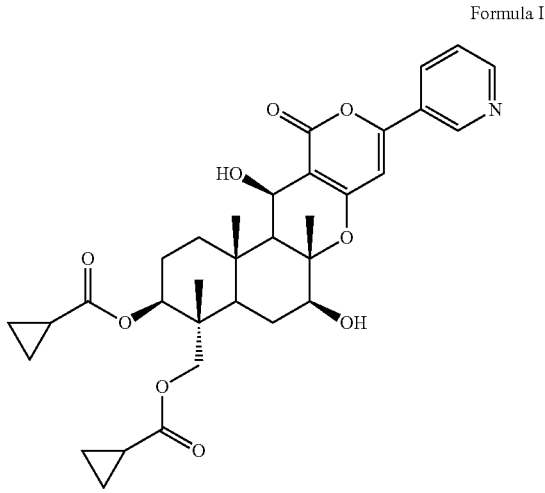

Formula I which, in an X-ray powder diffractogram at 25° C. and Cu—K$_\alpha$ radiation, shows at least four of the following reflexes, given as 2θ values: 7.5±0.2°, 9.6±0.2°, 11.0±0.2°, 11.7±0.2°, 12.1±0.2°, 12.5±0.2°, 15.8±0.2°, 16.3±0.2°, 17.4±0.2°, 19.3±0.2° and 19.6±0.2°.

23. A method for protecting plants from attack or infestation by insects, acarids or nematodes comprising contacting the plant, or the soil or water in which the plant is growing, with a composition according to claim 1 in pesticidally effective amounts.

24. A method for controlling insects, arachnids or nematodes comprising contacting an insect, acarid or nematode or their food supply, habitat, breeding grounds or their locus with a composition according to claim 1 in pesticidally effective amounts.

25. A method for protection of plant propagation material comprising contacting the plant propagation material with a composition as defined in claim 1 in pesticidally effective amounts.

* * * * *